US008333748B2

(12) United States Patent
Desai et al.

(10) Patent No.: US 8,333,748 B2
(45) Date of Patent: Dec. 18, 2012

(54) OUTER COVER FOR A DISPOSABLE ABSORBENT ARTICLE

(75) Inventors: Fred Naval Desai, Fairfield, OH (US); Khalid Qureshi, Mason, OH (US); Donald Carroll Roe, West Chester, OH (US)

(73) Assignee: The Procter & Gamble Company, Cincinnati, OH (US)

(*) Notice: Subject to any disclaimer, the term of this patent is extended or adjusted under 35 U.S.C. 154(b) by 702 days.

(21) Appl. No.: 12/398,615

(22) Filed: Mar. 5, 2009

(65) Prior Publication Data
US 2010/0228212 A1 Sep. 9, 2010

(51) Int. Cl.
*A61F 13/15* (2006.01)
*A61F 13/20* (2006.01)

(52) U.S. Cl. ......... 604/385.22; 604/385.01; 604/385.27; 604/385.24

(58) Field of Classification Search .................. 604/367, 604/385.01, 385.16, 385.22, 385.27–385.3
See application file for complete search history.

(56) References Cited

U.S. PATENT DOCUMENTS

| 3,692,618 | A | 9/1972 | Dorschner et al. |
| 3,802,817 | A | 4/1974 | Matsuki et al. |
| 3,848,594 | A | 11/1974 | Buell |
| 3,860,003 | A | 1/1975 | Buell |
| 3,911,173 | A | 10/1975 | Sprague |
| 3,929,135 | A | 12/1975 | Thompson |
| 4,116,892 | A | 9/1978 | Schwarz |
| 4,200,963 | A | 5/1980 | Kamfe et al. |
| 4,209,563 | A | 6/1980 | Sisson |
| 4,223,063 | A | 9/1980 | Sabee |
| 4,324,246 | A | 4/1982 | Mullane et al. |
| 4,340,563 | A | 7/1982 | Appel et al. |
| 4,342,314 | A | 8/1982 | Radel et al. |
| 4,438,167 | A | 3/1984 | Schwarz |
| 4,463,045 | A | 7/1984 | Ahr et al. |
| 4,515,595 | A | 5/1985 | Kievit et al. |
| 4,525,407 | A | 6/1985 | Ness |
| 4,573,986 | A | 3/1986 | Minetola et al. |
| 4,609,518 | A | 9/1986 | Curro et al. |
| 4,610,678 | A | 9/1986 | Weisman et al. |
| 4,629,643 | A | 12/1986 | Curro et al. |
| 4,662,875 | A | 5/1987 | Hirotsu et al. |
| 4,673,402 | A | 6/1987 | Weisman et al. |
| 4,695,278 | A | 9/1987 | Lawson |

(Continued)

FOREIGN PATENT DOCUMENTS

EP    1 559 388 A2    8/2005

(Continued)

OTHER PUBLICATIONS

PCT International Search Report, PCT/US2010/026041 date of mailing Jul. 1, 2010.

*Primary Examiner* — Michele M Kidwell
(74) *Attorney, Agent, or Firm* — Kathleen Y. Carter; John G. Powell

(57) ABSTRACT

An outer cover for a disposable absorbent article including waist regions elastically stretchable in the cross machine direction and activated in the cross machine direction, activated leg cuff regions elastically stretchable in one or more directions other than the cross machine direction, and an inelastic crotch region having a nonwoven crotch patch for providing the outer cover with suitable tensile strength, opacity, and poke-through properties.

15 Claims, 12 Drawing Sheets

U.S. PATENT DOCUMENTS

| | | | |
|---|---|---|---|
| 4,785,996 A | 11/1988 | Ziecker et al. |
| 4,795,454 A | 1/1989 | Dragoo |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,892,536 A | 1/1990 | DesMarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,968,312 A | 11/1990 | Khan |
| 4,990,147 A | 2/1991 | Freeland |
| 5,006,394 A | 4/1991 | Baird |
| 5,037,416 A | 8/1991 | Allen et al. |
| 5,062,840 A | 11/1991 | Holt et al. |
| 5,092,861 A | 3/1992 | Nomura et al. |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,171,236 A | 12/1992 | Dreier et al. |
| 5,202,173 A | 4/1993 | Wu et al. |
| 5,221,274 A | 6/1993 | Buell et al. |
| 5,246,433 A | 9/1993 | Hasse et al. |
| 5,254,111 A | 10/1993 | Cancio et al. |
| 5,260,345 A | 11/1993 | DesMarais et al. |
| 5,269,775 A | 12/1993 | Freeland et al. |
| 5,296,184 A | 3/1994 | Wu et al. |
| 5,306,266 A | 4/1994 | Freeland |
| 5,330,458 A | 7/1994 | Buell et al. |
| 5,342,338 A | 8/1994 | Roe |
| 5,354,597 A | 10/1994 | Capik et al. |
| 5,366,782 A | 11/1994 | Curro et al. |
| 5,387,207 A | 2/1995 | Dyer et al. |
| 5,397,318 A | 3/1995 | Dreier |
| 5,422,172 A | 6/1995 | Wu |
| 5,439,458 A | 8/1995 | Noel et al. |
| 5,460,622 A | 10/1995 | Dragoo et al. |
| 5,514,121 A | 5/1996 | Roe et al. |
| 5,518,801 A | 5/1996 | Chappell et al. |
| 5,540,671 A | 7/1996 | Dreier |
| 5,554,142 A | 9/1996 | Dreier et al. |
| 5,569,234 A | 10/1996 | Buell et al. |
| 5,571,096 A | 11/1996 | Dobrin et al. |
| 5,607,760 A | 3/1997 | Roe |
| 5,609,587 A | 3/1997 | Roe |
| 5,625,222 A | 4/1997 | Yoneda et al. |
| 5,626,571 A | 5/1997 | Young et al. |
| 5,635,191 A | 6/1997 | Roe et al. |
| 5,643,588 A | 7/1997 | Roe et al. |
| 5,650,214 A | 7/1997 | Anderson et al. |
| 5,653,703 A | 8/1997 | Roe et al. |
| 5,865,823 A | 2/1999 | Curro |
| 5,897,545 A | 4/1999 | Kline et al. |
| 5,938,648 A | 8/1999 | LaVon et al. |
| 5,941,864 A | 8/1999 | Roe |
| 5,957,908 A | 9/1999 | Kline et al. |
| 5,968,025 A | 10/1999 | Roe et al. |
| 5,977,430 A | 11/1999 | Roe et al. |
| 5,997,520 A | 12/1999 | Ahr et al. |
| 6,013,063 A | 1/2000 | Roe et al. |
| 6,120,487 A | 9/2000 | Ashton |
| 6,120,489 A | 9/2000 | Johnson et al. |
| 6,168,584 B1 | 1/2001 | Allen et al. |
| 6,169,151 B1 | 1/2001 | Waymouth et al. |
| 6,177,607 B1 | 1/2001 | Blaney et al. |
| 6,258,308 B1 | 7/2001 | Brady et al. |
| 6,368,444 B1 | 4/2002 | Jameson et al. |
| 6,432,098 B1 | 8/2002 | Kline et al. |
| 6,436,080 B1 | 8/2002 | Carlucci et al. |
| 6,476,289 B1 | 11/2002 | Buell et al. |
| 6,518,378 B2 | 2/2003 | Waymouth et al. |
| 6,521,555 B1 | 2/2003 | Bodaghi et al. |
| 6,555,643 B1 | 4/2003 | Rieger |
| 6,559,262 B1 | 5/2003 | Waymouth et al. |
| 6,680,265 B1 | 1/2004 | Smith et al. |
| 6,680,422 B2 | 1/2004 | Roe |
| 6,716,441 B1 | 4/2004 | Osborne et al. |
| 6,766,817 B2 | 7/2004 | da Silva |
| 6,794,023 B1 | 9/2004 | Melik et al. |
| 6,811,643 B2 | 11/2004 | McAmish et al. |
| 6,821,612 B1 | 11/2004 | Melik et al. |
| 6,843,949 B2 | 1/2005 | Brady et al. |
| 6,918,404 B2 | 7/2005 | Dias da Silva |
| 6,926,704 B2 | 8/2005 | Andersson et al. |
| 6,936,039 B2 | 8/2005 | Kline et al. |
| 7,056,411 B2 | 6/2006 | Desai et al. |
| 7,066,586 B2 | 6/2006 | da Silva |
| 7,169,288 B2 | 1/2007 | Drapeau |
| 7,201,822 B2 | 4/2007 | Schneider et al. |
| 7,222,654 B2 | 5/2007 | Schneider et al. |
| 7,223,818 B2 | 5/2007 | Autran et al. |
| 7,368,027 B2 | 5/2008 | Schneider |
| 2002/0105110 A1 | 8/2002 | Dobrin et al. |
| 2002/0112276 A1 | 8/2002 | Ruman et al. |
| 2003/0225382 A1 | 12/2003 | Tombult-Meyer et al. |
| 2003/0233082 A1 | 12/2003 | Kline et al. |
| 2004/0002691 A1 | 1/2004 | Popp et al. |
| 2004/0039364 A1 | 2/2004 | Karami |
| 2004/0092677 A1 | 5/2004 | Hanke et al. |
| 2004/0116028 A1 | 6/2004 | Bryner |
| 2004/0167486 A1 | 8/2004 | Busam et al. |
| 2004/0181200 A1 | 9/2004 | Desai et al. |
| 2004/0193133 A1 | 9/2004 | Desai et al. |
| 2004/0222553 A1 | 11/2004 | Desai et al. |
| 2004/0224132 A1 | 11/2004 | Roe et al. |
| 2004/0238105 A1 | 12/2004 | Schneider et al. |
| 2005/0070866 A1 | 3/2005 | Isele et al. |
| 2005/0164586 A1 | 7/2005 | Autran et al. |
| 2005/0165173 A1 | 7/2005 | Autran et al. |
| 2005/0211368 A1 | 9/2005 | McGuire et al. |
| 2005/0214461 A1 | 9/2005 | Desai et al. |
| 2005/0215963 A1 | 9/2005 | Autran et al. |
| 2005/0215964 A1 | 9/2005 | Autran et al. |
| 2005/0230034 A1 | 10/2005 | Arora et al. |
| 2006/0014460 A1 | 1/2006 | Isele et al. |
| 2006/0155253 A1 | 7/2006 | Dziezok et al. |
| 2006/0155254 A1 | 7/2006 | Sanz et al. |
| 2007/0078427 A1 | 4/2007 | Raycheck et al. |
| 2007/0093769 A1 | 4/2007 | Kline et al. |
| 2008/0004591 A1 | 1/2008 | Desai et al. |
| 2008/0215025 A1 | 9/2008 | Schneider |
| 2008/0224351 A1 | 9/2008 | Curro et al. |
| 2009/0127742 A1 | 5/2009 | Qureshi |
| 2009/0130242 A1 | 5/2009 | Qureshi |
| 2009/0131901 A1 | 5/2009 | Desai |
| 2010/0318054 A1 * | 12/2010 | Langdon et al. ......... 604/385.25 |

FOREIGN PATENT DOCUMENTS

| | | |
|---|---|---|
| EP | 1 600 132 A1 | 11/2005 |
| WO | WO 94/14395 A1 | 7/1994 |
| WO | WO 95/16746 A1 | 6/1995 |
| WO | WO 95/24173 A2 | 9/1995 |
| WO | WO 98/14156 A | 4/1998 |
| WO | WO 00/29199 A1 | 5/2000 |
| WO | WO 03/072338 A1 | 9/2003 |
| WO | WO 2005/110748 A1 | 11/2005 |
| WO | WO 2008/067463 A1 | 6/2008 |

* cited by examiner

OUTER COVER FOR A DISPOSABLE ABSORBENT ARTICLE

FIELD OF THE INVENTION

Disclosed herein are absorbent articles and stretchable outer covers used therewith. More specifically, materials and methods for providing various stretchable outer cover configurations having different directions of stretch in different portions of the outer cover are disclosed.

BACKGROUND OF THE INVENTION

Wearable absorbent articles (e.g., taped diapers, pull-on diapers, training pants, incontinence briefs) offer the benefit of receiving and containing urine and/or other bodily exudates of a wearer. Wearable absorbent articles typically include an absorbent core assembly for storing the bodily exudates positioned between a liquid pervious topsheet and a liquid impermeable backsheet. While such absorbent articles may be suitable for meeting a basic need of exudate containment, some wearers of disposable absorbent articles and/or the caregivers of such wearers may desire a disposable absorbent article that provides increased comfort to the wearer and/or is more aesthetically pleasing, for example, by including features typically associated with cotton underwear.

Cotton underwear generally includes cotton fibers suitable for making soft, relatively strong material (i.e., cloth). Cotton underwear is typically configured to exhibit low-force stretch and good recovery (i.e., the material is extensible when a relatively low amount of force is applied and returns substantially to its prestrain shape/size when the force is removed), especially in the waist regions of the underwear, which are typically required to stretch laterally across the upper pelvic, lower abdominal, and/or upper buttocks regions of a wearer, when the wearer is physically active (e.g., walking, running, and/or crawling). In addition to stretchable waist regions, cotton underwear may also include elastic waist and/or leg bands. The elastic waist and/or leg bands may encircle the waist and/or legs of the wearer to provide 360-degree stretch around the waist and/or legs. Unlike some disposable articles, however, cotton underwear is typically not designed to accommodate large discharges of bodily waste from wearers. Additionally, cotton underwear is generally not used as a "disposable" article (i.e., intended to be discarded after relatively few uses rather than laundered and reused). Further, cotton underwear tends to be more expensive than a disposable diaper.

Despite the problems that may be associated with cotton underwear, at least some manufacturers of disposable absorbent articles desire to provide a disposable absorbent article that includes one or more of the desirable features of cotton underwear. To this end, the manufacturer may include an outer cover on the disposable article that is formed from a material having the look and feel of cloth. The manufacturer may also form the outer cover to have elastic properties similar to those of underwear. For example, it is known in the art that an extensible polyethylene-containing nonwoven may be joined with an elastic material (e.g., nonwoven, film, or strand) to form an elastic laminate, and then subjected to an activation process (sometimes referred to as incremental stretching). The extensible polyethylene-containing nonwoven is typically used to provide the desired softness to the laminate. After the laminate is subjected to a suitable activation process, the elastic material may be capable of providing the desired elasticity. Examples of elastic laminates include "zero-strain" stretch laminates (i.e., laminates formed by joining an extensible nonwoven to an untensioned elastic material and then subjecting the laminate to an activation process), stretch-bonded laminates, and necked-bonded laminates.

Examples of stretchable laminates and methods for making stretchable laminates may be found in: U.S. Pat. No. 4,116,892, titled "Process for Stretching Incremental Portions of an Orientable Thermoplastic Substrate and Product Thereof," to Schwarz; U.S. Pat. No. 4,834,741, titled "Diaper With Waistband Elastic," to Sabee; U.S. Pat. No. 5,156,793, titled "Method for Incrementally Stretching Zero Strain Stretch Laminate Sheet In A Non-Uniform Manner To Impart A Varying Degree Of Elasticity Thereto," to Buell et al.; U.S. Pat. No. 5,167,897, titled "Method for Incrementally Stretching A Zero Strain Stretch Laminate Sheet To Impart Elasticity Thereto," to Webber et al.; and U.S. Pat. No. 5,422,172, titled "Elastic Laminated Sheet of An Incrementally Stretched Nonwoven Fibrous Sheet and Elastomeric Film and Method," to Wu. However, polyethylene-containing nonwovens may not provide a suitable amount of material strength, or bond strength when joined to other absorbent article components. In addition, certain processes used to form outer covers for disposable absorbent articles may cause polyethylene-containing nonwovens to produce fuzz on the surface of the outer cover, which some users may find undesirable.

Another feature that manufacturers of disposable absorbent articles may include on a disposable absorbent article to make it more underwear-like is an elastic leg and/or waist opening configured to provide 360-degree stretch around the leg or waist of a wearer. The elastic leg and/or waist opening, when coupled with a cloth-like outer cover on a disposable absorbent article, may provide an article with, e.g., reduced gapping between the absorbent article and the leg of the wearer and/or improved containment of exudates stored in the disposable absorbent article. The elastic material used to form a leg and/or waist opening may be joined to an activated portion of a nonwoven outer cover so that the soft, cloth-like material to which the leg band is joined does not impede or "lock up" the stretchability of the elastic leg band (i.e., inhibit the leg band from stretching over its full range). In this way, the leg opening of the disposable absorbent article can extend further than the "virgin" (i.e., unactivated) nonwoven material, and thereby fit a wider range of wearer leg sizes than some traditional leg opening configurations. However, due to the tradeoff between unactivated and activated material properties (e.g., opacity versus strength), some manufacturers of disposable absorbent articles may limit how much of the leg opening portion of the outer cover is activated (e.g., how far the activated portion extends laterally inward). If the leg band is positioned too close to the nonactivated leg opening portion of the outer cover or if the activated portion of the outer cover is too narrow (relative to the width of the leg band), the extensibility of the leg opening may still be restricted, resulting in an undesirable fit in the leg opening area of the disposable absorbent article.

Activating an extensible material typically subjects portions of the material to relatively high strain and/or strain rates, which may result in undesirable changes to the thickness, opacity, strength, and/or other physical properties of the material. Insufficient opacity may result in the undesirable visibility of the wearer's skin or bodily exudates stored in the absorbent article, and insufficient strength may result in the finger of a caregiver or foot of a wearer penetrating one or more layers of the outer cover (i.e., "poke-through"). In addition, certain materials that provide a desirable amount of softness such as polyethylene-containing nonwovens may not have a suitable level of strength. On the other hand, certain materials that provide a desirable level of strength such as polypropylene nonwovens may not provide a suitable amount of softness. Including an elastomeric material in the outer cover of an underwear-like absorbent article may reduce at least some of the undesirable effects related to activation by providing increased opacity, decreased "set" (i.e., permanent deformation resulting when a material is extended, then allowed to relax) induced by the activation process, and/or structural strength (e.g., in areas of the article where the nonwoven may have been weakened by the activation process). However, elastomeric film materials tend to be relatively expensive compared to the nonwoven materials typically used in absorbent article outer covers. Therefore, the elastomeric film material may be present only in areas of the outer cover where elasticity is most desired (e.g., waist regions and/or leg band regions) as opposed to including a full-length elastomeric film material. The absence of an elastomeric film in the leg band region of the outer cover may require a reduction in the amount of activation in this area (e.g., reduced depth of engagement of the intermeshing teeth of the activation apparatus) to maintain a desirable level of material strength or integrity. Reducing the amount of activation, however, may result in an increase in the amount of force required to stretch the leg band region of the outer cover to fit the desired range of wearer sizes, which may further reduce the range of wearer sizes.

One way to address the problems of low opacity and/or strength is to include one or more additional full-coverage (i.e., length and width) layers of nonwoven material to the outer cover and/or increase the basis weight of the single, full-coverage layer of nonwoven material. The additional full-coverage layer(s) of nonwoven and/or higher basis weight nonwovens may overcome at least some of the problems associated with low opacity and low strength and may even be cheaper than a full-coverage elastic film. However, there may still be an undesirable increase in the cost of producing the outer cover. In addition, some disposable absorbent articles may include graphics and other indicia on the outer cover (e.g., popular cartoon characters, letters, numbers, and/or shapes), which are commonly printed or embossed onto the inner and/or outer facing surface of the outer cover. The additional layers of nonwoven and/or higher basis weight material in the outer cover may undesirably obscure the graphics (e.g., the graphics may be distorted and/or less vibrant).

Another problem that may be encountered when providing a cloth-like, stretchable outer cover for a disposable absorbent article is that the properties (e.g., thermal and/or chemical) of the various outer cover components may not complement each other or even be compatible. For example, in order to provide a suitable cloth-like outer cover it may be desirable to securely join leg bands to the outer cover. The leg bands may be made from a material that provides good softness (e.g., polyethylene based). However, it may be undesirable to fabricate the entire outer cover from polyethylene due to cost or other factors. In this instance, the leg band and the outer cover may be formed from different materials that impart desired properties to each component of the absorbent article. Due to the different chemical/thermal properties of the outer cover material and the leg band material, suitable bonds (e.g., high pressure or thermal bonds) may not be formed between the leg band and the outer cover, potentially resulting in a poor quality absorbent article. Thus, it may be problematic to directly couple various absorbent article components to one another due to the differences in the chemical and/or thermal properties of the outer cover and component materials.

Accordingly, it would be desirable to provide a reduced cost disposable absorbent article with the look and feel of cotton underwear. It would also be desirable to provide an outer cover with improved structural integrity and opacity in the crotch region. It would further be desirable to provide an absorbent article that has an outer cover with relatively unobscured graphics. It would additionally be desirable to decouple the bond strength of components bonded the outer cover from the chemistry of the outer cover material.

SUMMARY OF THE INVENTION

In order to provide a solution to the problems set forth above, at least one embodiment herein discloses a stretchable outer cover for a disposable absorbent article. The outer cover comprises a longitudinal direction, a lateral direction, a first longitudinal side edge and a second longitudinal side edge opposed thereto, a garment facing side and an opposing wearer facing side, a first waist region and a second waist region opposed thereto. A portion of at least one of the first and second waist regions is activated in the lateral direction. The outer cover further comprises a crotch region disposed between the first and second opposing waist regions and a leg band portion disposed adjacent to at least one of the first and second longitudinal side edges in at least the crotch region. The leg band portion is activated in a direction other than the lateral direction. The outer cover further comprises an extensible nonwoven base layer. The base layer is coextensive with the outer cover in at least the longitudinal direction. The outer cover also comprises an extensible nonwoven reinforcing member joined to the base layer. The reinforcing member is disposed in at least the leg band portion in at least the crotch region of the outer cover. The outer cover also comprises an elastic leg band joined to at least one of the base layer and the reinforcing member in the leg band portion of the outer cover. The outer cover also comprises at least one intermittent elastic layer joined to the nonwoven base layer in at least the first and second waist regions. The elastic layer(s) is absent in at least a portion of the crotch region.

DETAILED DESCRIPTION

Figure 1:
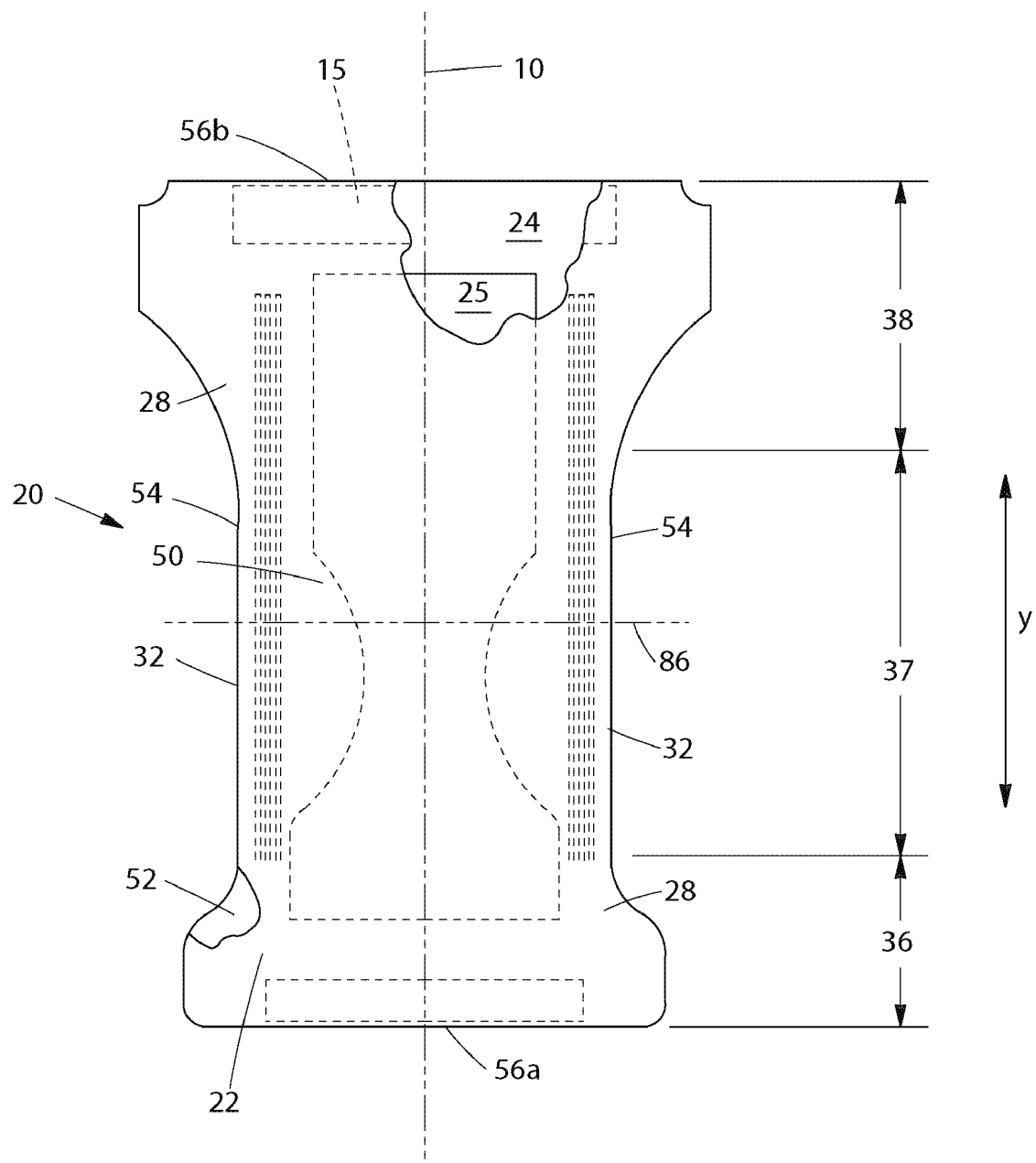
FIG. 1 is a plan view of an outer cover.

Definitions:

"Absorbent article" means an article that absorbs and/or contains liquid. Wearable absorbent articles are absorbent articles placed against or in proximity to the body of the wearer to absorb and contain various exudates discharged from the body. Nonlimiting examples of wearable absorbent articles include diapers, pant-like or pull-on diapers, training pants, sanitary napkins, tampons, panty liners, incontinence devices, and the like.

"Activation" is the mechanical deformation of one or more portions an extensible material (e.g., film, nonwoven, fiber) that results in permanent elongation of the extensible material in the direction of activation in the X-Y plane of the material. Activation of a laminate that includes an elastic material joined to an extensible material typically results in one or more portions of the extensible material being permanently elongated, while the elastic material returns substantially to its original dimension. During a typical activation process, an extensible material is incrementally stretched by engaging it between two rolls or plates that have a multitude of three dimensional, complementary, interengaging surface features such as teeth and grooves. "Level of Activation" means the amount that a material has been activated based on the maximum distance of overlap between complementary, intermeshing surface features on opposing rolls/plates when the rolls/plates are engaged. A higher level of activation corresponds to a larger overlap distance. "Activated" means a material has been subjected to an activation process. Suitable examples of absorbent articles, absorbent article components and processes for activation can be found in U.S. Pat. Nos. 5,156,793; 4,438,167; 5,202,173; 5,254,111; 5,296,184; 5,354,597; 6,258,308; 6,368,444; 6,811,643; 6,821,612; 6,843,949; and 6,794,023.

"Direction of Activation" means the direction in which the material is stretched in the X-Y plane during the activation process. For laminates comprising elastic materials laminated to inelastic nonwovens or films, the direction of activation is also the direction in which the laminate is capable of stretching after completion of the activation process. For materials that do not exhibit elastic behavior, the direction of activation refers to the direction of the dimension in the X-Y plane of the material that is increased most as a result of the activation process. Examples of directions of activation include, without limitation, machine direction, cross machine direction, longitudinal direction, lateral direction, and diagonal direction.

"Disposed" means the placement of one element of an article relative to another element of an article. For example, the elements may be formed (joined and positioned) in a particular place or position as a unitary structure with other elements of the diaper or as a separate element joined to another element of the diaper.

"Elastic" means the property of a material or component (e.g., film, fiber, nonwoven, strand, laminate or combinations of these) to elongate, without rupture or breakage, by at least 50% at a load of between 0.1 and 10 N/cm in the Hysteresis Test. Further, upon release of the load, the elastic material or component has set less than or equal to 20% as measured according to the Hysteresis Test. For example, an elastic material that has an initial length of 25 mm can elongate to at least 37.5 mm (50% elongation) and, upon removal of the force, retract to a length of 27.5 mm, i.e., have a set of 2.5 mm (10% set). It is to be understood, however, that this definition of elastic does not apply to materials such as individual elastic strands that do not have the proper dimensions (e.g., not wide enough) to be properly subjected to the hysteresis test. Instead, such material is considered to be elastic if it can elongate to at least 50% upon application of a biasing force, and return substantially to its original length (i.e., exhibit less than 20% set) upon release of the biasing force.

"Extensible" material is material that elongates, without rupture or breakage, by at least 50% at a load of between 0.1 and 10 N/cm in the Hysteresis Test. Further, upon release of the load, the material has set greater than 20% as measured according to the Hysteresis Test. For example, an extensible material that has an initial length of 25 mm can elongate at least to 37.5 mm (50% elongation) and, upon removal of the applied force, retract to a length of 35 mm, i.e., have a set of 10 mm (40% set), when subjected to the Hysteresis Test.

"Film" means a substantially nonporous material made by a process that includes extrusion of, e.g., a polymeric material through a relatively narrow slot of a die. A film may be impervious to a liquid and pervious to an air vapor, but need not necessarily be so. Suitable examples of films are described in more detail hereinbelow.

"Garment-facing side" means the outermost portion of an element of a wearable absorbent article when the absorbent article is worn as intended. The opposing side, or innermost portion, of the same element is referred to as the "wearer-facing side." It is to be understood that the garment-facing side and the wearer-facing side of an element are relative to the wearer of the article with the garment-facing side being furthest from the wearer and the wearer-facing side being closest to the wearer. In the example of a typical disposable diaper, the portion of the outer cover that faces away from the wearer is the garment-facing side while the opposing side of the outer cover is the wearer-facing side.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by methods known in the art, e.g. adhesive bonding, thermal bonding, ultrasonic bonding, or high pressure bonding using non-heated or heated patterned roll.

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the web in a manufacturing process. Directions within 45 degrees of the MD are considered to be machine directional. The "cross machine direction" or "CD" is the direction substantially perpendicular to the MD and in the plane generally defined by the web. Directions within 45 degrees of the CD are considered to be cross directional.

"Nonwoven" means a porous, fibrous material made from continuous (long) filaments (fibers) and/or discontinuous (short) filaments (fibers) by processes such as spunbonding, meltblowing, carding, and the like. Nonwovens do not have a woven or knitted filament pattern. Nonwovens may be liquid permeable or impermeable.

"Outboard" and "inboard" mean, respectively, to the location of an element disposed relatively far from or near to the longitudinal centerline of an absorbent article with respect to a second element. For example, if element A is outboard of element B, then element A is farther from the longitudinal centerline than is element B.

"Strain" means to stretch a material beyond an initial length. A method for calculating "percent strain" is given in the Hysteresis Test Method below.

"Stretchable" material is material that elongates, without rupture or breakage, by at least 50% at a load of between 0.1 and 10 N/cm in the Hysteresis Test. A stretchable material may be elastic or extensible as defined herein.

"Unactivated" means a material or portion thereof has not been subjected to a mechanical deformation process that permanently elongates the material.

"Web" means a material capable of being wound into a roll. Webs may be films, nonwovens, laminates, apertured laminates, and the like. The face of a web refers to one of its two dimensional surfaces, as opposed to its edge.

"X-Y plane" means the plane defined by the MD and CD of a moving web or the length and width of a piece of material.

Outer Cover

Disposable absorbent articles such as disposable diapers are generally designed to provide a suitable fit around the waist and legs of a wearer. Ideally, a disposable absorbent article would provide the same kind of fit as cotton underwear (e.g., all-over low-force stretch to fit a relatively wide range of wearer sizes and shapes). In addition to the benefits of comfort and fit, an underwear-like disposable article may also receive and store one or more insults of bodily excrement without leakage. The underwear-like disposable absorbent article may further provide desirable opacity and strength in at least the crotch region of the article so that excrement contained in the article is not visible to the wearer of the article and/or the caregiver of the wearer from outside the article, and the possibility of poke-through is at least reduced. Surprisingly, it is believed that such an absorbent article may be provided by configuring the outer cover of the absorbent article to have portions activated in different directions, and by providing a reinforcing member in the crotch region of the outer cover for improved opacity and/or strength.

An absorbent article and/or an outer cover for use in a disposable article, as disclosed herein, may include front and rear waist regions that correspond to those areas of the absorbent article disposed on the upper pelvic, lower abdominal, and/or upper buttocks regions of a wearer when the article is worn as intended. The outer cover may also include a crotch region that corresponds to the portion of the article generally positioned between the legs of the wearer when the article is worn as intended. Each region may be roughly one-third of the longitudinal length of the article, or any other length as desired. The regions may be the same or a different longitudinal length relative to one or more of the other regions. The crotch portion generally encompasses the lateral axis of the outer cover. The "lateral axis" is an imaginary line extending in the lateral direction that bisects the outer cover into symmetrical portions. In certain embodiments, the waist regions may correspond to the portion of the absorbent article that is laterally disposed between the side seams of an article when it is in a fastened configuration (i.e., the article is fastened, refastened, or prefastened). The waist and crotch regions, except for those portions included in the leg band portion and buffer zone (described in more detail below), are collectively referred to herein as the body portion of the outer cover. In certain embodiments, the outer cover may include a leg band portion for joining a leg band thereto. The leg band portion is generally disposed on one or both of the longitudinal side edges of the outer cover e.g., 60 mm, 50 mm, 40 mm, 30 mm, 20 mm, 10 mm, 5 mm (or any value in the range of between 5 mm and 60 mm) inboard of the side edge. The leg band portion may be disposed entirely in the crotch region or extend longitudinally into one or both waist regions of the outer cover. In certain embodiments, it may be desirable to configure the leg band portion to encircle the leg opening that is formed when the absorbent article is in a fastened configuration. One or more portions, or even all, of the leg band portion may be coterminous with the side edge of the outer cover, but need not necessarily be so. The leg band portion may be configured to extend linearly in the longitudinal direction, curvilinearly along the contour of the outer cover side edge, and/or any other direction, as desired.

The cloth-like outer cover disclosed herein may be a single layer of material or a laminate of two or more layers of material. The outer cover may include a base layer configured as an outer, wearer-facing side of the outer cover and the absorbent article. The base layer may be configured to be a relatively thin, low basis weight layer, which contributes to a relatively lightweight, thin outer cover. For example, the base layer may have a basis weight of between 10 and 50 g/m$^2$. The base layer may be configured to have a caliper of between 0.05 and 1 mm, under a pressure of 2100 Pascals. Calipers for both film and nonwoven materials described herein may be determined according to ASTM D5729-97 (2004), titled "Standard Test Method for Thickness of Nonwoven Fabrics." The base layer may be selected to provide a soft, cloth-like feel and may include one or more extensible nonwoven materials. For example, the base layer may be formed from a single layer of spunbond and/or meltblown polyolefin fibers (e.g., a polyethylene-containing nonwoven or any other suitable material known in the art). In certain embodiments, the base layer may include one or more webs of polypropylene/polyethylene blends. Blends of polyethylene and polypropylene may be provided in any suitable weight % based on the weight of the blend. For example, a blend may include weight percent ratios of 30/70, 50/50, 60/40, 70/30, 80/20 (polypropylene/polyethylene). The blends may be in the form of core/sheath-type bicomponent fibers (i.e., fibers that have an outer sheath of a first composition surrounding an inner core of a second composition) or side-by-side bicomponent fibers. Nonwovens made of polypropylene/polyethylene core/sheath bicomponent fibers may be configured to provide a web having a desired combination of softness, strength, and extensibility. The ratio of polypropylene and polyethylene in the core and sheath can be tailored to give the desired properties. One particularly suitable example of material for use as a soft, outer base layer is a spunbond nonwoven made from core/sheath type bicomponent fibers that include 70% polypropylene in the core and 30% polyethylene in the sheath, available from Fiberweb plc, Simpsonville, S.C. under the trade name SOFTEX. The base layer may also be a spunbond web comprising polypropylene or polyethylene monocomponent fibers. In another example, the base layer may be a spunbond-meltblown-spunbond polyolefin fibrous web that includes mono and/or bicomponent fibers. In yet another example, the base layer may include a monocomponent or bicomponent carded web.

The outer cover may also include an elastic layer. The elastic layer may be joined to the base layer by any means known in the art, e.g., adhesive bonding, ultrasonic bonding, thermal calendar bonding, high pressure bonding. The elastic layer may be intermittent (i.e., discontinuous) in one or more directions. For example, a longitudinally intermittent elastic layer may be present in a portion of one or both waist regions of the outer cover, but absent in at least a portion of the crotch region. In certain embodiments, the elastic layer may be coextensive with one or both waist regions in the longitudinal and/or lateral direction. In certain embodiments, the intermittent elastic layer may be formed from a single piece (or laminate) of elastic material that is substantially coextensive with only the body portion of one or both waist regions. In certain embodiments, a laterally intermittent elastic layer may be present in a portion of one or both side panel regions of an outer cover, but absent in at least a portion of the body region inboard of the side panel regions. In certain embodiments, the intermittent elastic layer may be both longitudinally and laterally intermittent. In certain embodiments, the elastic layer may be present as one or more elastic strips that extend laterally across the outer cover in a portion of one or both waist regions. The elastic layer may extend partially into the crotch region, however, it may be desirable to limit the extent to which the elastic layer extends into the crotch region to, e.g., limit the cost of producing the outer cover. The elastic layer may be exemplified as an elastic film, however, it is to be understood that the elastic layer may include one or more layers of elastic film(s), elastic nonwoven(s), and/or elastic strand(s), or laminates of elastic materials and extensible materials. For example, the elastic layer may be a bilaminate formed by joining the elastic layer to an extensible nonwoven layer, and then subjecting the bilaminate to an activation process to enable the laminate, for example, to stretch in at least the lateral direction. Alternatively or additionally, the bilaminate may be joined to the base layer and then subjected to an activation process. In another example, the elastic layer may be configured as a trilaminate, in which an elastic material layer is sandwiched between two extensible nonwoven layers, or between a nonwoven layer and a film layer. As with the bilaminate example, the trilaminate may be subjected to an activation process before, during, and/or after being joined to the base layer. Certain elastic materials suitable for use herein may have some amount of "tack" (i.e., stickiness), and thus may exhibit undesirable characteristics when wound onto and/or unwound from a roll (e.g., high unwind force and/or relatively noisy). In order to at least partially reduce the tendency of the tacky elastic material to stick to itself when wound onto a roll, another material (e.g., nontacky polymeric material) may be disposed on the surface(s) of the elastic material to act as a so-called "skin." The skin may at least partially mask the undesirable tackiness of the elastic material. It may be desirable to provide a relatively thin, lightweight outer cover, and therefore suitable basis weights for the elastic layer described herein may range from e.g., 10 to 100 grams per square meter ("gsm"), 15 to 75 gsm, or even 20 to 50 gsm. The skin basis weight may be from 2-10 gsm or 3-5 gsm. Suitable elastic layer calipers may range from, e.g., 0.01 to 0.1 mm. One particularly suitable example of an elastic material for use in the outer cover 500 is a 25 gsm elastic polypropylene film comprising VISTAMAXX, an elastomeric polypropylene resin available from ExxonMobil Chemical, Houston, Tex.

Because the elastic layer is generally not present in at least a portion of the crotch region of the outer cover, the structural integrity, opacity, and/or other characteristics of the outer cover in the crotch region may be undesirably impacted. To compensate for any such deficiencies, the basis weight of the outer cover base layer may be increased, but as pointed out above this may undesirable increase manufacturing costs and/or diminish the clarity and vibrancy of the graphics. Therefore, it may instead be desirable to include a reinforcing member disposed generally in the crotch region of the outer cover. The reinforcing member may be made from the same material as the base layer or any other suitable material known in the art, e.g., an extensible nonwoven material. While film materials may be functionally suitable for use as a reinforcing member, the lack of underwear-like characteristics typically exhibited by film materials (e.g., softness, texture, and breathability) may make the use of certain films undesirable. The underwear-like characteristics of films may be acceptably enhanced by techniques such as mechanical activation or hydroaperturing or vacuum forming/aperturing.

The reinforcing member may extend the full longitudinal and/or lateral length of the crotch region and even into one or both waist regions; however, it may be desirable to limit the extent to which the reinforcing member extends into a waist region to reduce any undesirable results that may be associated with such a configuration (e.g., increased cost and/or reduced extensibility). In order to provide a reinforcing member that does not undesirably increase the cost and/or complexity of manufacturing an outer cover, it may be desirable to select a suitable shape and size for the reinforcing member. For example, the reinforcing member may comprise one or more rectangular shaped pieces of material laminated together or joined with one another along one or more edges. The reinforcing member may be configured to have a surface area of between 20 and 60%, 25 and 50%, or even between 30 and 40% of the surface area of the wearer-facing side of the base layer. It is to be understood that the reinforcing member is not limited to any particular shape or size, but may be any suitable shape, as desired. The reinforcing member may be joined to the wearer-facing side or the garment-facing side of the outer cover; however, when the reinforcing member is placed on the garment-facing side of the outer cover, the reinforcing member may undesirably interfere with the visibility of any graphics disposed on the garment-facing surface of the outer cover. In certain embodiments, the reinforcing member may overlap and be joined to the wearer-facing side or the garment-facing side of the elastic layer in one or both waist regions. In certain embodiments, the reinforcing member may include two or more discrete webs positioned longitudinally and/or laterally intermittent from one other. The basis weight of the reinforcing member material may be selected to increase the opacity of the outer cover and/or increase the strength of the outer cover (i.e., increase the outer cover's resistance to poke through or tearing). Suitable basis weights for a nonwoven reinforcing member may be between 10 and 50 grams per square meter. Suitable peak loads for the nonwoven reinforcing member may be between 3 N/cm and 30 N/cm or between 5 and 20 N/cm, when measured according to the Tensile Test. In certain embodiments, the material of the reinforcing member may be selected to decouple the chemical properties of the base layer from the chemical properties of one or more components joined to the base layer. For example, it is believed, without being limited by theory, that a component made of polypropylene and a component made of polyethylene may not have suitable bond strength when bonded to one another with, e.g., high pressure and/or thermal bonds due to a difference in melting temperature and/or other material properties. As a result, it may be necessary to sacrifice an undesirable amount of the soft, cloth-like property provided by the polyethylene in order to obtain a desirable amount of bonding strength provided by the polypropylene, or vice versa, for example, in embodiments wherein a leg band and/or other component having a relatively high polyethylene content (e.g., for softness and/or stretch) is bonded to an outer cover having a relatively high polypropylene content (e.g., for strength). Therefore, it may be desirable to form the outer cover components from materials that are blends of different compositions (e.g., blends of polypropylene and polyethylene). When two blended materials are bonded together (e.g., thermally), it is believed that the total basis weight of each composition in the combined substrate may contribute to the strength of the bond between the two blended materials. Thus, changing the basis weight of the reinforcing member and/or the basis weight percent of the polyethylene in the reinforcing member may provide suitable strong bonds between the base layer and other components (e.g., leg bands) joined to the base layer when such components are bonded to one another. Examples 1-14 are provided below to further illustrate this concept.

The outer cover may include one or more leg bands joined to the wearer-facing side or the garment-facing side of the base layer in the leg band portion of the outer cover. The leg band may be positioned in the leg band portion of the outer cover, as desired. For example, the leg band may be coterminous with the leg band portion (or activated leg band portion) of the base layer along the longitudinal side edge of the outer cover or the leg band may be disposed inboard of the side edge. The leg band may include a soft, cloth-like material (e.g., polyethylene-containing nonwoven or film) on its outer surface to provide a disposable absorbent article cover with the look and feel of cotton underwear. The leg band may be an elastic leg band, for example, configured as a zero-strain stretch laminate or a "live-stretch" laminate (i.e., the elastic material is at least partially extended when it is joined to an extensible nonwoven or film). An elastic leg band may be configured as a single layer of elastic material joined to the outer cover, or as laminate material. The leg band may include elastic elements, such as strands or other leg band materials, joined to the wearer-facing surface of the base layer or the elastic layer of the outer cover; however, it is to be understood that the leg band may include one or more elastic elements and not be an elastic leg band. In certain embodiments, the reinforcing member may cover the wearer-facing surface of any elastic elements present in the leg band. In certain embodiments, the elastic elements may be joined and/or sandwiched between one or more layers of the outer cover, (e.g., the base layer and the reinforcing member) to form an elastic leg band. When the leg band includes an activated nonwoven, the nonwoven may be subjected to an activation process before, during, and/or after being incorporated into the leg band. In certain embodiments, the nonwoven may be subjected to an activation process after the leg band is joined to the outer cover. For example, the leg band (and any nonwoven present in the leg band) may be subjected to a first activation process prior to being incorporated into an outer cover, and then subjected to second activation process after being joined to the outer cover.

The outer cover may also include a waist band attached to the outer cover in one or both waist regions. The waist band may be elastic and may be formed from the same material as the leg band(s). In certain embodiments, the waist band may be joined to the garment-facing side of the outer cover in order to help provide a disposable absorbent article with an underwear-like look and feel. The waist band may be configured to be structurally similar or even the same as the leg bands (e.g., bilaminate, trilaminate, skins, elastic films, elastic nonwovens, elastic strands). The waist band may extend fully or partially around the circumference of a waist opening formed when the disposable absorbent article is in a fastened configuration. The waistband may alternatively be joined to the wearer-facing side of the outer cover or sandwiched between layers of the outer cover.

In certain embodiments, the waist band and/or the leg band may be prestretched prior to attaching them to any other layer of the outer cover. Prestretching may provide contracted waist and/or leg bands that respectively encircle the waist and legs of the baby and make the product more underwear like.

In order to provide a cloth-like outer cover, it may be desirable to activate one or more portions of the base layer and/or reinforcing member, which include an extensible material, in one or more directions. For example, the leg band portion of the base layer may be activated in the longitudinal direction over substantially its entire length and/or surface area. In another example, the leg band portion may be activated along a curvilinear path that follows the contour of the longitudinal side edge. The leg band portion may be activated at different depths (i.e., the activation rolls or other apparatus used to activate the leg band portion may be configured to have different depths of engagement) and/or in different directions, as desired. In certain embodiments, the leg band portion may include an outboard sub-region and an inboard sub-region. The outboard sub-region may be activated to a greater extent (i.e., exhibit greater extensibility in the direction of activation for a given applied force) than the inboard sub-region. The outboard sub-region may be activated such that it is able to extend as far as or farther than an elastic leg band that may be attached to the leg band region of the outer cover without showing any significant signs of material failure (e.g., tearing). Additionally or alternatively, it may be desirable to activate the outboard sub-region such that when the outboard sub-region is stretched to a particular length (or circumference in the case of a leg opening of a diaper), it acts to prevent the leg band region, and any leg band joined thereto, from extending past an extension which may cause damage (i.e., a substantial increase in applied force is required for further extension). The inboard sub-region may be activated to a lesser extent than the outboard sub-region or may even be nonactivated. The inboard sub-region may be coextensive in one or more directions and/or contiguous with the outboard sub-region, but need not necessarily be so. The inboard and outboard sub-regions may individually or collectively have a continuum of levels of activation that extend from a region of relatively high activation at the outboard portion of the sub-region(s) to a region of relatively low activation at the inboard portion of the subregion(s). Any or all of the base layer, elastic material, leg band, and reinforcing member may be activated separately before combining and/or together after combining. An absorbent article that includes the outer cover of this example may have a full range of stretch in the leg opening when the article is worn by a wearer, and simultaneously exhibit desirable material properties as demonstrated by, e.g., improved opacity, reduced sagging, and/or reduced poke-through. In traditional disposable absorbent articles, portions of the outer cover that are adjacent to and inboard of the leg band portion of the outer cover may be unactivated or activated in a direction other than the direction of activation of the leg band portion. It is known that abrupt changes in the direction of activation, rate of activation, and/or level of activation may damage a material during the activation process (e.g., pinholing or tearing). Therefore, it may be desirable to activate the outboard sub-region and inboard sub-region at different depths.

All or part of the base layer disposed in the body portion of the outer cover may be activated, e.g., in the lateral direction or any other direction, as desired. It may be desirable to have the portion of the base layer disposed in the body portion of the crotch region of the outer cover remain unactivated. By not activating in the crotch region, the strength, opacity, and/or other material properties may be improved compared to an outer cover that includes an activated base layer in the body portion of the crotch region. The portion(s) of the outer cover that include the elastic layer joined to an activated portion of the base layer may desirably exhibit low force, recoverable stretch, e.g., by elongating to 50% strain under a load of less than 2 N/cm, 1.5 N/cm, or even less than 1 N/cm and having set of less than 20%, 15%, even less than 10%, according to the Hysteresis Test.

Figure 2:
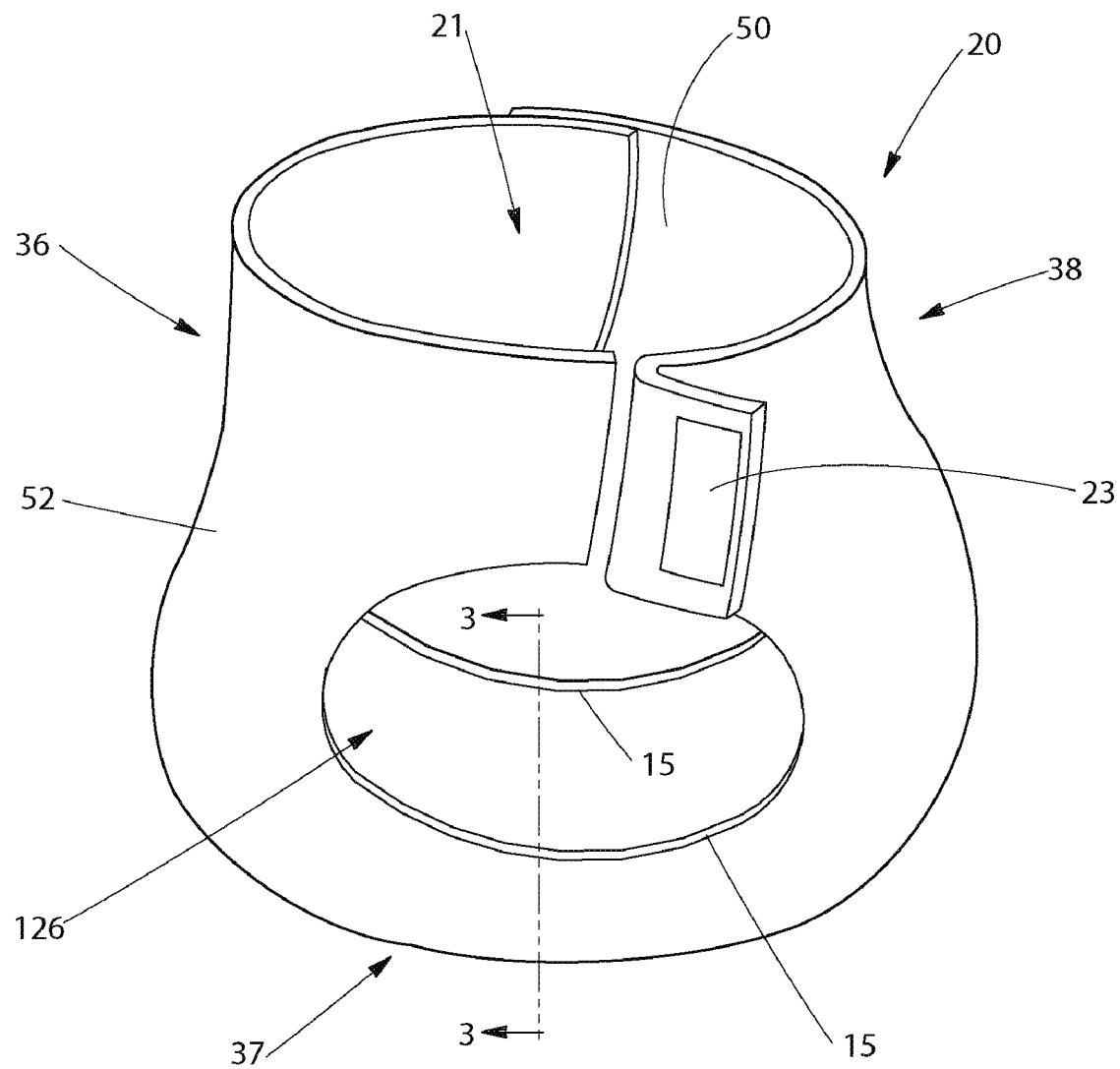
FIG. 2 is a perspective view of a disposable absorbent in a fastened configuration.

FIG. 1 shows a partial cut-away view of a diaper 20. The diaper 20 shown in FIG. 1 is in a flat-out, uncontracted state (e.g., with no elastic induced contraction). The diaper 20 may include a liquid pervious topsheet 22; an outer cover 24 joined with the topsheet 22; an absorbent core assembly 26 positioned between the topsheet 22 and the outer cover 24; side panels 28; and leg bands 32. The diaper 20 may further include an outer, garment-facing surface 52 opposed to an inner, wearer-facing surface 50, a front waist region 36, a back waist region 38 opposed to the front waist region 36, and a crotch region 37 positioned between the front and back waist regions 36 and 38. The front and back waist regions 37 and 38 may include the region of the diaper 20 where the front and back portions of the diaper 20 are connected to form a garment, as shown in FIG. 2. The front and back waist regions 36 and 38 may each include one or more elastic waist features 15 configured to stretch in the lateral direction 4 when a force is applied to the front and/or back waist region 36, 38. The elastic waist feature 15 may encircle the waist opening 21 of the diaper 20 when the diaper 20 is in a fastened configuration, as shown in FIG. 2. The diaper 20 may include longitudinal edges 54, a first end edge 56A in the front waist region 36, and a longitudinally opposed second end edge 56B in the back waist region 38. The diaper 20 may include a longitudinal centerline 10 (e.g., positioned midway between the longitudinal side edges 54) and a lateral centerline 86 (e.g., positioned midway between opposing end edges 56A and 56B) orthogonal thereto. The absorbent core assembly 26 may be configured to receive and store bodily excrement. The absorbent core assembly 26 may include one or more acquisition layers, distribution layers, storage layers, core cover layers, dusting layers, and/or barrier cuffs. The absorbent core assembly 26 may include any suitable absorbent material known in the art such as, for example, cellulose fibers and/or superabsorbent polymer materials. In certain embodiments, the absorbent core assembly 26 may be configured as a so-called bucket-shaped absorbent core assembly 26, which is explained in more detail below. As used herein, "bucket-shaped" refers to the appearance of a lateral cross section of the absorbent core assembly 26 when the diaper 20 is configured as it would be when applied to a wearer (see, e.g., FIGS. 2-3). Suitable examples of absorbent core assemblies 26 and bucket-shaped absorbent core assemblies 26 are described in U.S. Publication No. 2008/0004591, titled "Absorbent Article Having An Anchored Core Assembly," filed by Desai, et al., Jun. 7, 2007.

FIG. 2 shows the disposable diaper 20 of FIG. 1 in a fastened configuration, i.e., the front waist region 26 and the back waist region 28 are joined together to form waist opening 21. The diaper 20 may include a fastening system 23 or bond region for temporarily or permanently securing the front and back waist regions 26 and 28 of the diaper 20 together to form the waist opening 21. The diaper 20 may include one or more leg openings 126 defined by the leg band region 15. The leg opening 126 may have a minimum hoop diameter of, e.g., at least 4 cm, and a maximum hoop diameter of, e.g., at least 20 cm. The leg opening 126 may be configured to have a range of hoop diameters whereby the maximum hoop diameter is at least 3×, 5× or even 10× greater than the minimum hoop diameter.

Figure 3:
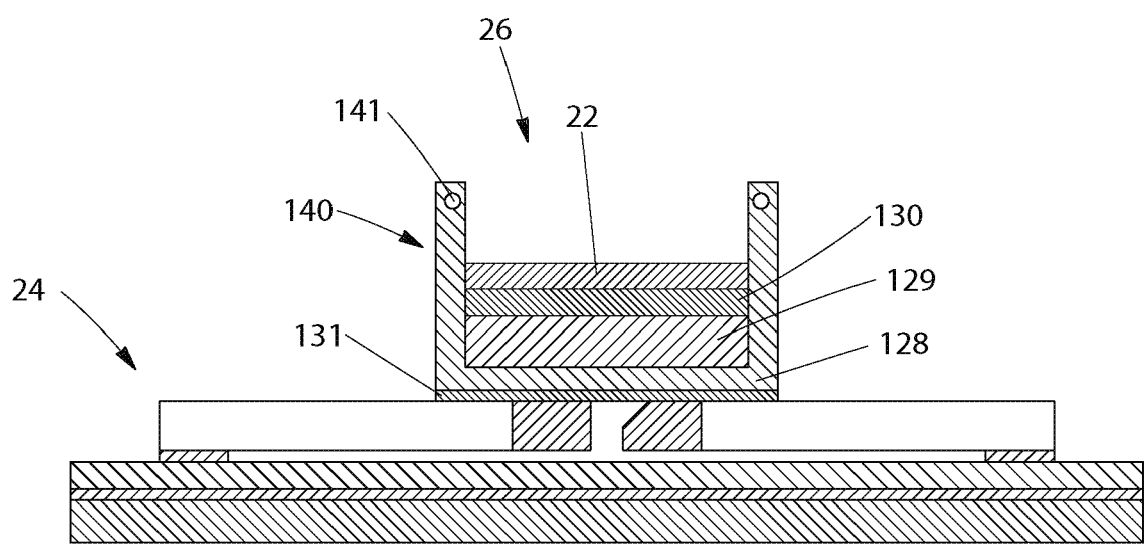
FIG. 3 is a cross-section view an absorbent assembly.

FIG. 3 is cross-section view of the diaper 20 of FIG. 2 along line 3-3 illustrating a bucket-shaped absorbent assembly 26. The bucket-shaped absorbent core assembly 26 may be configured as a substantially self-contained absorbent core assembly 26. For example, the bucket-shaped absorbent core assembly 26 may include a topsheet 22, a containment member 128 (e.g., liquid impermeable, breathable film layer), one or more of the absorbent core elements described above (e.g., core cover layer 130, absorbent material layer 129), and/or one or more pairs of leg cuffs 140 (e.g., inner cuff or barrier leg cuffs) including one or more elastic elements 141. The absorbent core assembly 26 may be joined to the outer cover 24 by any suitable means known in the art, e.g., by adhesive 131.

Figure 4:
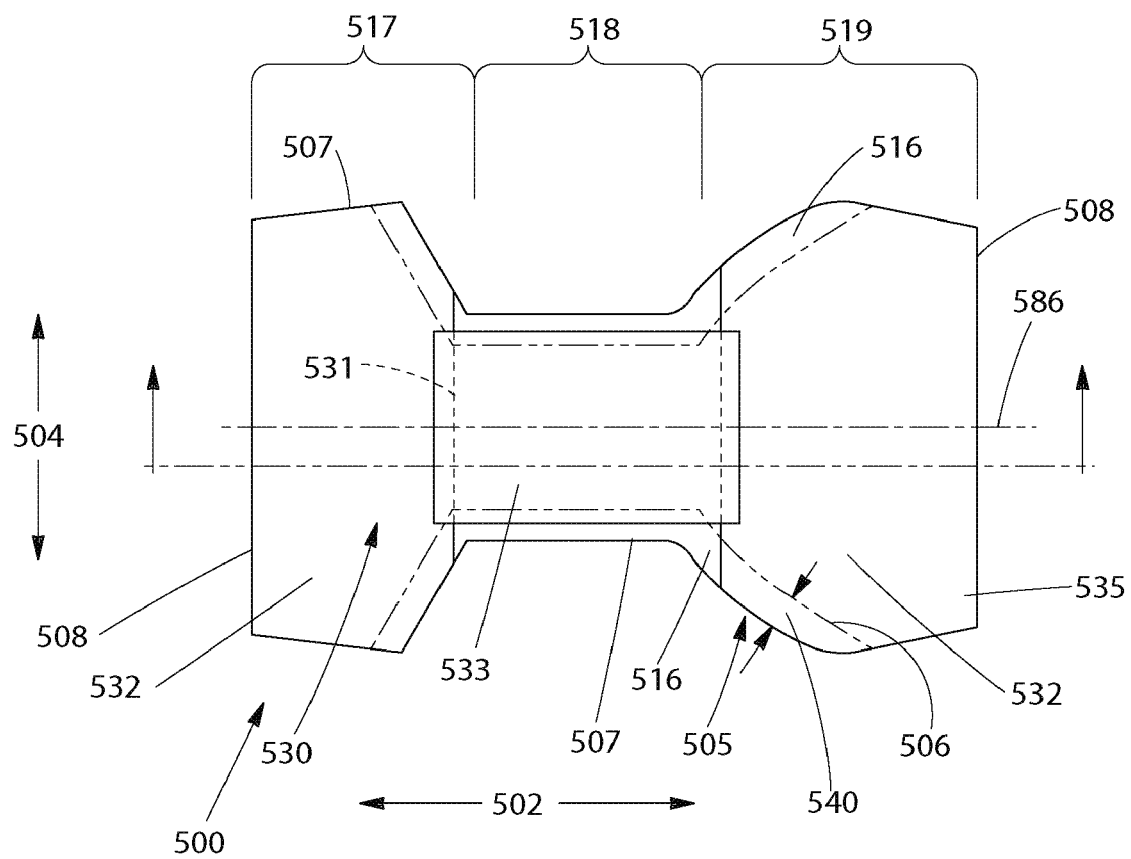
FIG. 4 is a plan view of an outer cover.

FIG. 4 is an example of an embodiment of an outer cover 500. The outer cover 500 includes opposing side edges 507 positioned on opposite sides of longitudinal centerline 586 and opposing end edges 508. The outer cover 500 has a first waist region 517, a second waist region 519, and a crotch region 518 disposed therebetween. The outer cover 500 includes a body portion 530 and a leg band portion 516. The leg band portion 516 has a width 570, (i.e., the shortest distance between the inboard edge 506 and outboard edge 505 of the leg band portion 516) and may extend through the crotch region 518 and into one or both waist regions 517, 519. The leg band portion 516 may extend in any suitable direction as long as the leg band portion 516, when activated, provides the desired amount of stretch. For example, the leg band portion 516 may extend linearly in the lateral direction 504 in the crotch region 518 and diagonally or along a curvilinear path in one or both waist regions 517, 519. The outer cover 500 may include a continuous base layer 535 that is coextensive with the outer cover 500 in the longitudinal and lateral directions 502 and 504, respectively. The outer cover 500 may include an intermittent elastic layer 532. The intermittent elastic layer 532 may include an elastic material joined to the continuous base layer 535 in one or both waist regions 517 and 519. In certain embodiments, the intermittent elastic layer 532 may include an elastic material joined to an extensible nonwoven or film material to form an intermittent laminate (i.e., a laminate where the laminate is not continuous in one or more directions). The intermittent elastic layer 532 may be disposed in portions of the waist regions 517, 519, the crotch region 518, and/or the leg band region. In certain embodiments, the intermittent elastic layer 532 may have a first longitudinal edge 531 disposed in or near the crotch region 518 and a second longitudinal edge contiguous with an end edge 508 of the outer cover 500. The outer cover 500 may be configured to include a reinforcing member 533. The reinforcing member 533 may be disposed generally in the crotch region 518 of the outer cover 500 and inboard of or contiguous with a side edge 507. The reinforcing member 533 may be disposed in at least a portion of one or both waist regions 517, 519 and may be joined to the wearer-facing side 570 of the base layer 535 in the body portion 530 and, optionally, in the leg band portion 516. The reinforcing member 533 may be joined to the base layer 535 and/or the elastic layer 532. In certain embodiments, it may be desirable to partially or entirely exclude the elastic layer 532 and/or reinforcing member 533 from a particular portion(s) the leg band portion 516 in order to reduce the chance that one of these components may undesirable inhibit the stretch of the leg band portion 516 and/or any leg band that may be joined thereto.

Figure 5:
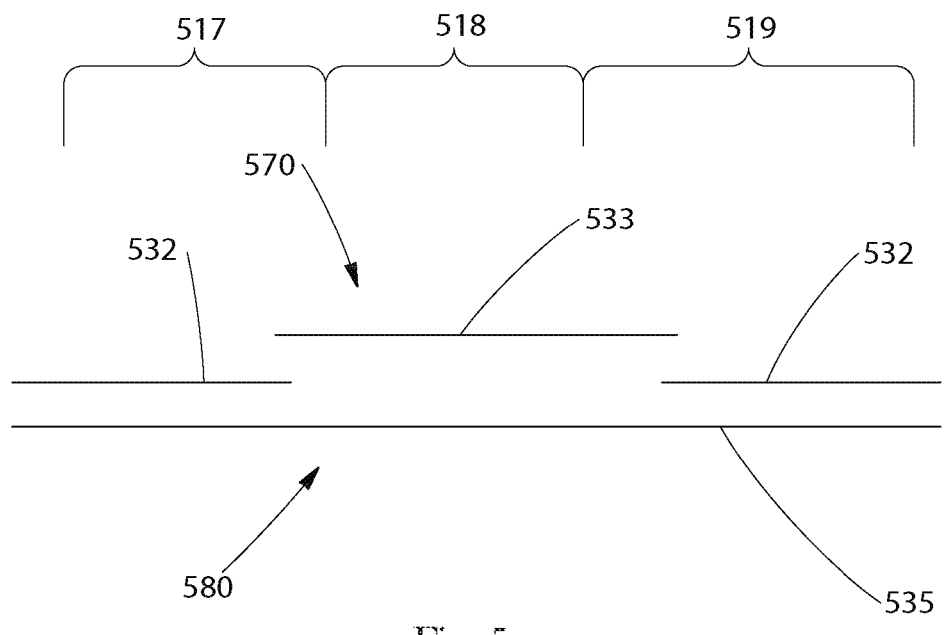
FIG. 5 is a cross-section view of the outer cover.

FIG. 5 shows a cross-sectional view of the outer cover 500 of FIG. 4 along line 5-5. As shown in FIG. 5, the outer cover 500 has a wearer-facing side 570 and an opposing garment-facing side 580. The intermittent elastic layer 532 is disposed in the front and back waist regions 517, 519, and joined to the base layer 535. The reinforcing member 533 is disposed in the crotch region 518, and may overlap the intermittent elastic layer 532 in the front and/or back waist regions 517, 519. In certain embodiments, the reinforcing member 533 and the elastic layer 532 may not overlap at all. The reinforcing member 533 may be joined to the elastic layer 532 in one or both waist regions 517, 519 and/or the base layer 535. In the example shown in FIG. 5, the reinforcing member 533 is disposed on the wearer-facing side 570 of the base layer 535 and the elastic layer 532. In certain embodiments, however, the reinforcing member 533 may be positioned on the wearer-facing side of the base layer 535 and on the garment-facing side 580 of the elastic layer 532.

Figure 6:
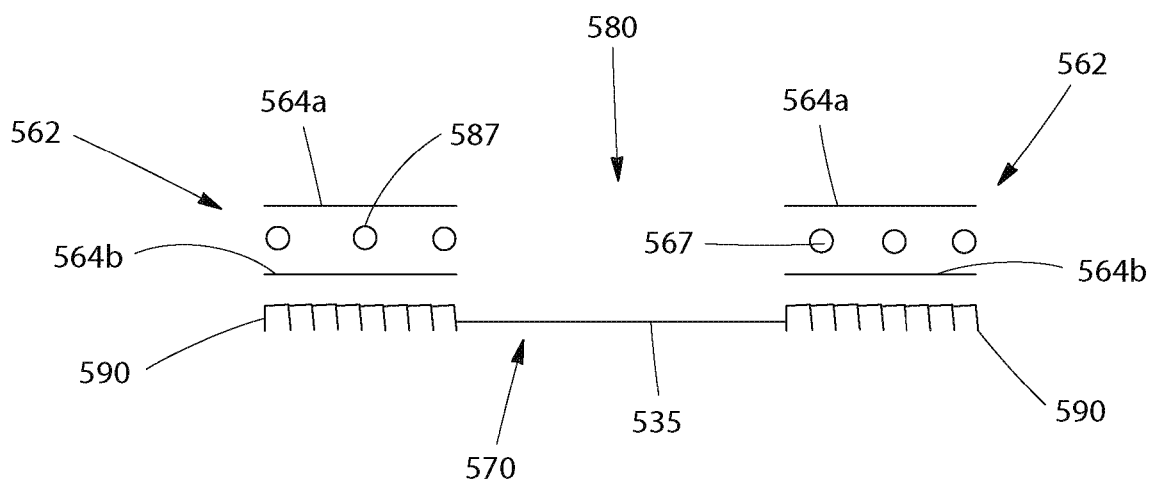
FIGS. 6-10 are cross-section views of examples of outer cover configurations.

FIG. 6 shows a cross-section view of an example of an embodiment of the outer cover 500 along line 6-6. The outer cover 500 may include one or more leg bands 562 joined to an activated portion 590 of the base layer 535 on the garment-facing side 580 of the outer cover 500. The leg band 562 may be coextensive with the activated portion 590 of the base layer 535, as shown in FIG. 6, but need not necessarily be so. The leg band 562 may include one or more elastic strand layers 567 sandwiched between an outer extensible film or nonwoven layer 564A and an inner extensible film or nonwoven layer 564B. The entire leg band or only portions thereof may be elastic. The inner extensible layer 564B may be joined to the base layer 535 via ultrasonic bonds, adhesive bonding, or high pressure bonding using heated or unheated patterned rolls, and/or any other suitable bonding means known in the art.

Figure 7:
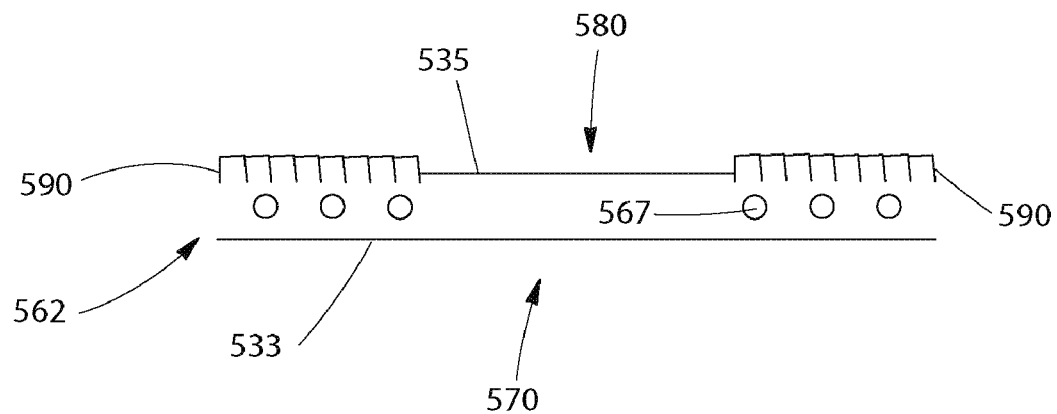

FIG. 7 shows a cross-section view of an example of an embodiment of the outer cover 500 along line 6-6. The outer cover 500 may include elastic leg bands 562 configured as one or more elastic strand layers 567 sandwiched between base layer 535 and the reinforcing member 533. The leg band 562 may be joined to the activated portion 590 of the base layer 535 on the wearer-facing side 580 of the outer cover 500 by joining (e.g., adhesively bonding) the elastic layer 567 and/or reinforcing member to the base layer 535 in the leg band portion 516 of the outer cover 500. Alternatively or additionally, the elastic layer 567 may be joined (e.g., adhesively) to the reinforcing member 533.

Figure 8:
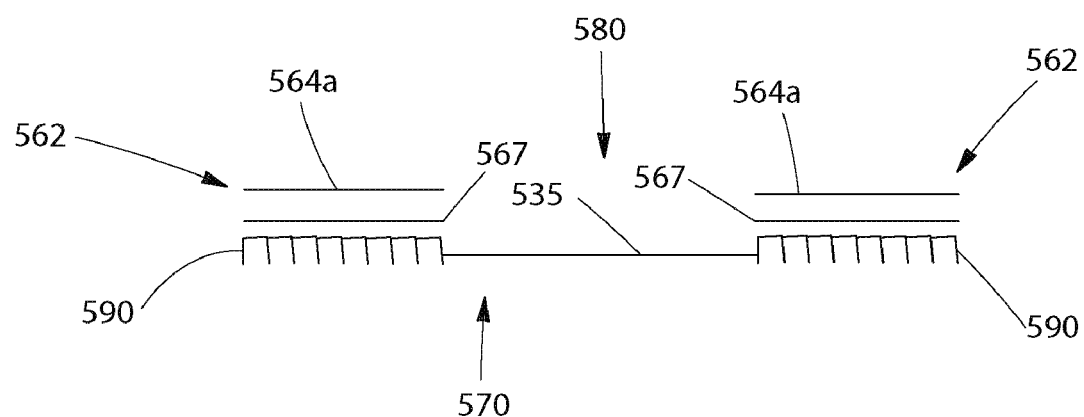

FIG. 8 shows a cross-section view of an example of an embodiment of the outer cover 500 along line 6-6. The outer cover 500 may include leg bands 562 configured as one or more elastic film and/or nonwoven layers 567 sandwiched between the outer extensible film or nonwoven layer 564A and the inner extensible film or nonwoven layer 564B. The leg band 562 may be joined to the activated portion 590 of the base layer 535 on the garment-facing side 580 of the outer cover 500 by bonding the elastic layer 567 to the base layer 535.

Figure 9:
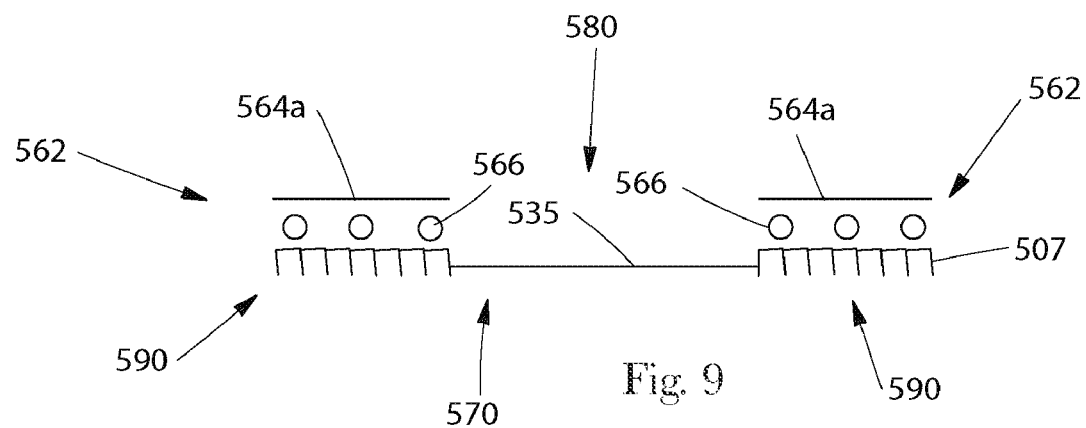

FIG. 9 shows a cross-section view of an example of an embodiment of the outer cover 500 along line 6-6. The outer cover 500 may include one or more leg bands 562 joined to the base layer 535 on the garment-facing side 580 of the outer cover 500. The leg band 562 may include one or more elastic strands 566 sandwiched between an outer extensible film or nonwoven layer 564A and the base layer 535.

Figure 10:
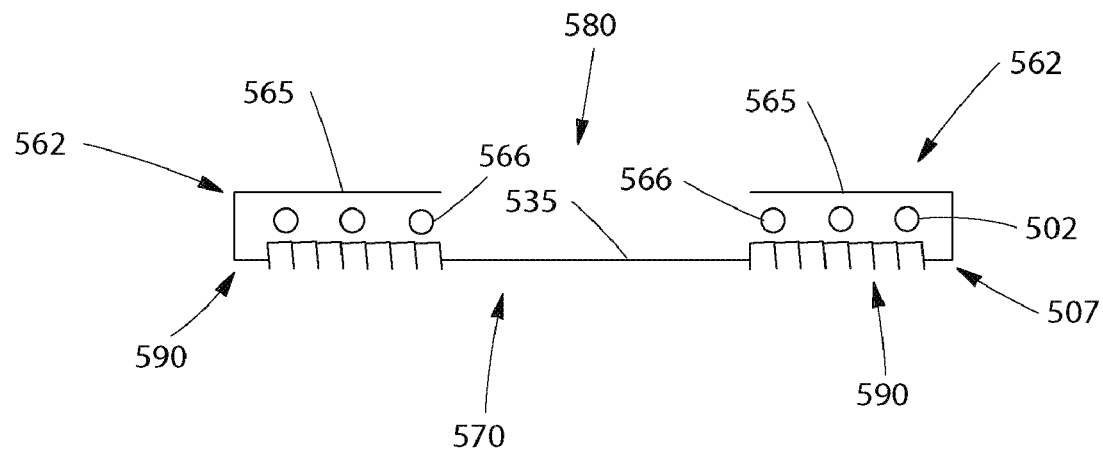

FIG. 10 shows an example of an embodiment of the outer cover 500 along line 6-6. The Elastic strands 566 or any other suitable elastic material or laminate may be joined to the activated portion 590 of the base layer 535 inboard of the side edge 507, such that a flap 565 is formed between the outboard edge 502 of the strands 566 and the side edge 507 of the base layer 535. The flap 565 may be folded over the strands 566 and bonded to itself or another component to form a sleeve-like structure that encloses the strands 566, as shown in FIG. 10. The flap 565 may be activated or unactivated, and/or may be subjected to an activation process at any suitable time during the formation of the outer cover 500 to provide a desirable amount of stretch to the leg band portion 516 of the outer cover 500.

Figure 11:
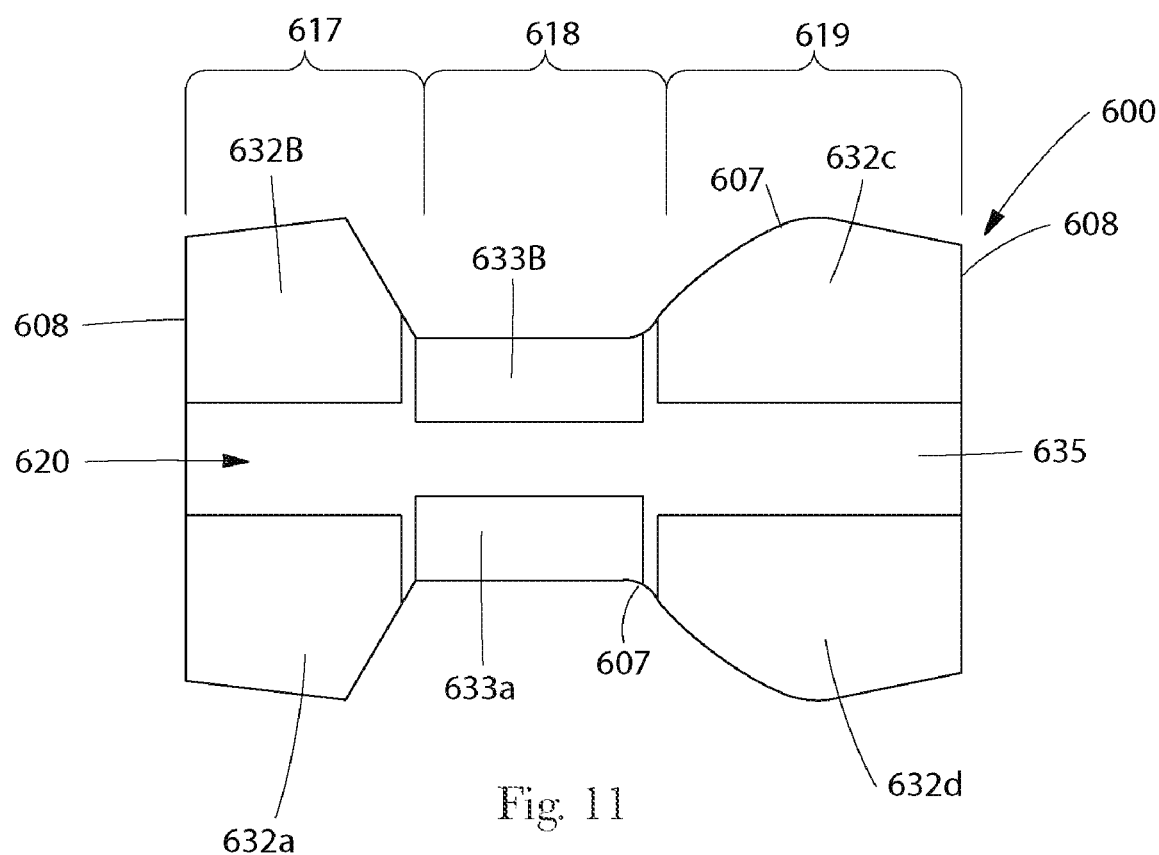
FIG. 11 is a plan view of an outer cover.

FIG. 11 is an example of an embodiment of an outer cover 600. The outer cover 600 includes opposing side edges 607 and opposing end edges 608. The outer cover 600 has a first waist region 617, a second waist region 619, and a crotch region 618 disposed therebetween. The outer cover may include a continuous base layer 635 that is coextensive with the outer cover 600 in the lateral and longitudinal directions. The outer cover 600 may include an elastic layer that is intermittent in the longitudinal and lateral directions and joined to the base layer 635. The elastic layer may include four elastic members 632A, 632B, 632C, and 632D disposed in four different portions of the outer cover 600. Two or more elastic members (e.g., 632A and 632B) may be disposed in the first waist region 617 and two or more elastic members (e.g., 632C and 632D) may be disposed in the second waist portion 619. Adjacent elastic members 632A and 632B or 632C and 632D may include a space 620 separating the elastic members 632A, 632B, 632C, and 632D in the lateral direction. It is to be understood that embodiments wherein two or more of the elastic members 632A, 632B, 632C, and 632D overlap one another in lateral and/or longitudinal direction are also contemplated herein. The lateral space 620 may have any dimensions desired as long as the waist regions 617 and/or 619 of the outer cover 600 exhibit suitable underwear-like stretch. One or more of the elastic members 632A, 632B, 632C, and 632D may extend into the crotch region 618 of the outer cover 600 and/or overlap one or more portions of the reinforcing member 533. The outer cover 600 may include a reinforcing member. The reinforcing member may include two or more reinforcing member webs 633A and 633B. The reinforcing member webs may be separated from one another in the lateral direction by any suitable distance as long as the crotch region 618 of the outer cover 600 exhibits desirable structural characteristics (e.g., opacity and strength).

Figure 12:
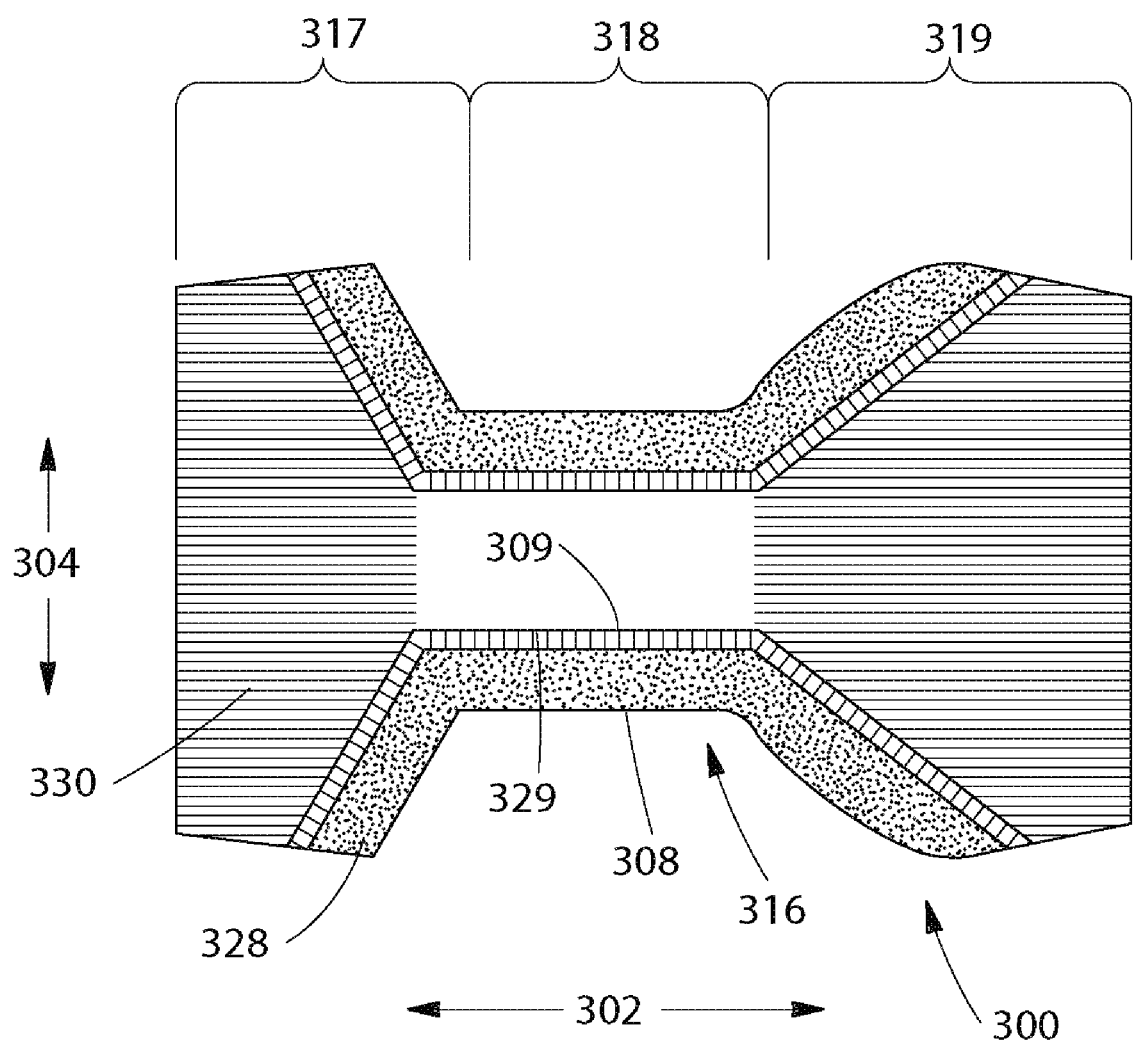
FIG. 12 is a plan view of an outer cover.

FIG. 12 shows an example of an embodiment of an outer cover 300. The outer cover has a lateral direction 304 and a longitudinal direction 302. The outer cover 300 includes a front waist region 317, a rear waist region 319 and a crotch region 318 disposed therebetween. The outer cover 300 may include a leg band portion 316 for attaching a leg band thereto. The leg band portion 316 has an outboard edge 308 and an inboard edge 309. The leg band portion 316 includes an outboard sub-region 328 and an inboard sub-region 329 disposed between the outboard sub-region 328 and the inboard edge 309. The leg band portion 316 may be activated in a longitudinal or curvilinear direction. The outer cover 300 shown in FIG. 10 is activated in the lateral direction in the first and second waist regions 317, 319. The crotch region 318 of the outer cover 300 may be nonactivated.

EXAMPLES

Figure 13:
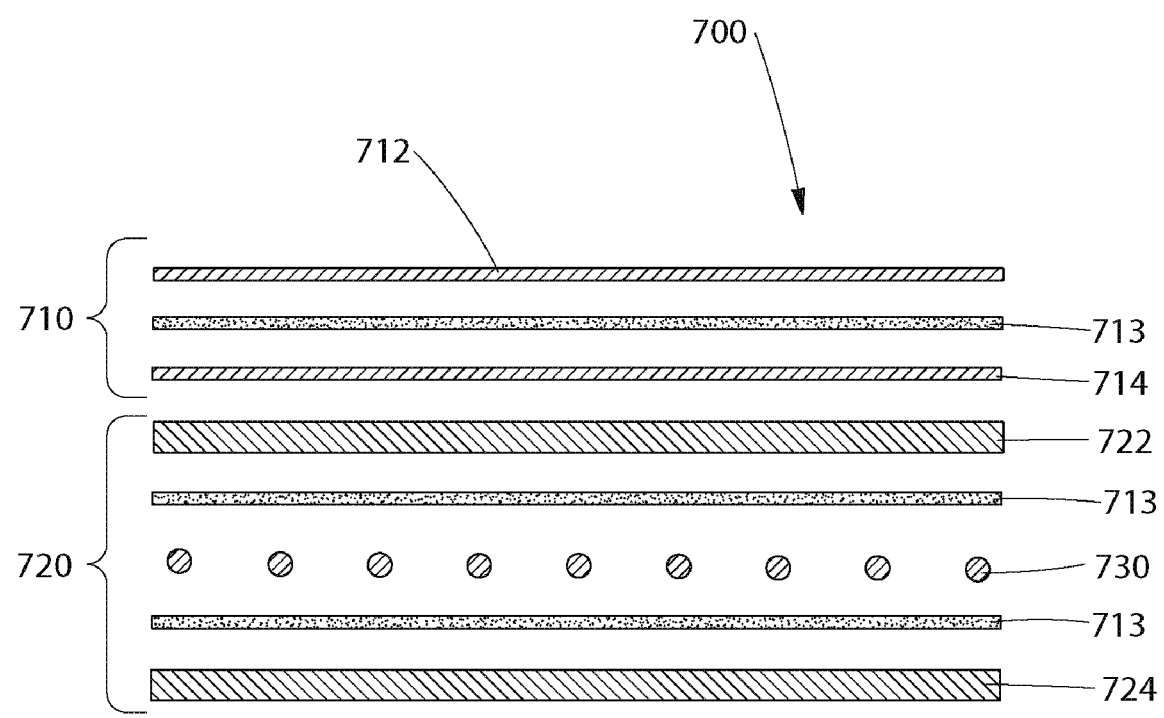
FIG. 13 is a cross-section view of a laminate structure.

The Examples below each comprise a laminate 700 constructed as shown in FIG. 13. The laminate 700 includes a first web 710 and second web 720. The examples illustrate the relationship of total basis and PE basis weight with respect to bond strength of a high pressure bond. The first web 710 includes a first nonwoven layer 712 joined to a second nonwoven layer 714 with 4.5 gsm of an adhesive 713 sold under the trade name ZeroCreep, available from Bostik Inc., Wauwatosa, Wis. The first and second nonwoven layers 712 and 714 are formed from core-sheath type bi-component fibers with the core of each fiber comprising polypropylene ("PP") and the sheath comprising polyethylene ("PE"). For each example, the total basis weight of the first and second nonwoven layers 712 and 714 and the basis weight percentages of PP and PE are shown in columns 2-5 of Table 1. The basis weight percentages of PP and PE are based on the total basis weight of the nonwoven. The second web 720 is a laminate that includes a first 100% PE film layer 722, a second 100% PE film layer 724, and an elastic strand layer 730 disposed between the first and second film layers 722 and 724. The layers of the second web 720 are joined together with 4.5 gsm of an adhesive 713 sold under the trade name ZeroCreep, available from Bostik Inc., Wauwatosa, Wis. The total basis weight of the two film layers is shown in column 6 of Table 1. In the present Examples, the basis weight of the individual film layers is the same, however embodiments wherein the film layers have different basis weights are contemplated herein. In Examples 1, 4-5 and 7, the first web 710 and the second web 720 are bonded together using a high pressure bonding process, such as is known in the art, using a nip pressure of 90,000 pounds per square inch. In Examples 2-3, 6 and 8-10, the first web 710 and the second web 720 are bonded together using a high pressure bonding process, such as is known in the art, using a nip pressure of 110,000 pounds per square inch. The nip pressure is calculated by dividing the pressure applied to the roll, which is sometimes referred to as "air-bag pressure" (e.g., 40 or 50 psi), over the total area of the outermost surface of the tips of the "nubs" on the surface of the roll. It is believed that the disclosed differences in nip pressure used to form the high pressure bonds does not significantly affect the bond strength in the disclosed Examples.

Figure 14A:
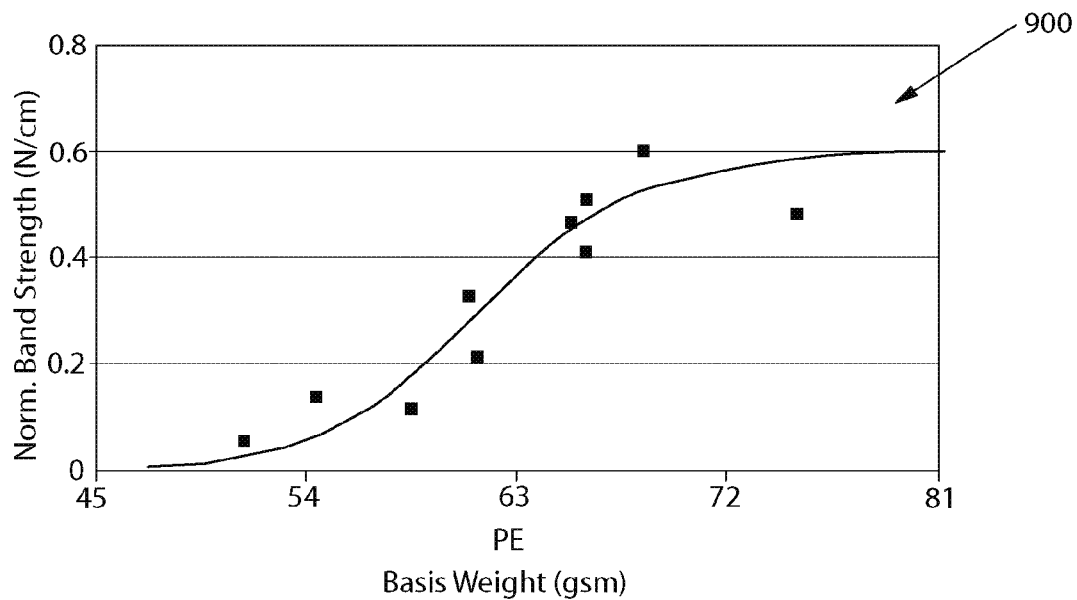
FIG. 14A is a representation of a graph depicting total polyethylene content versus normalized bond strength.
Figure 14B:
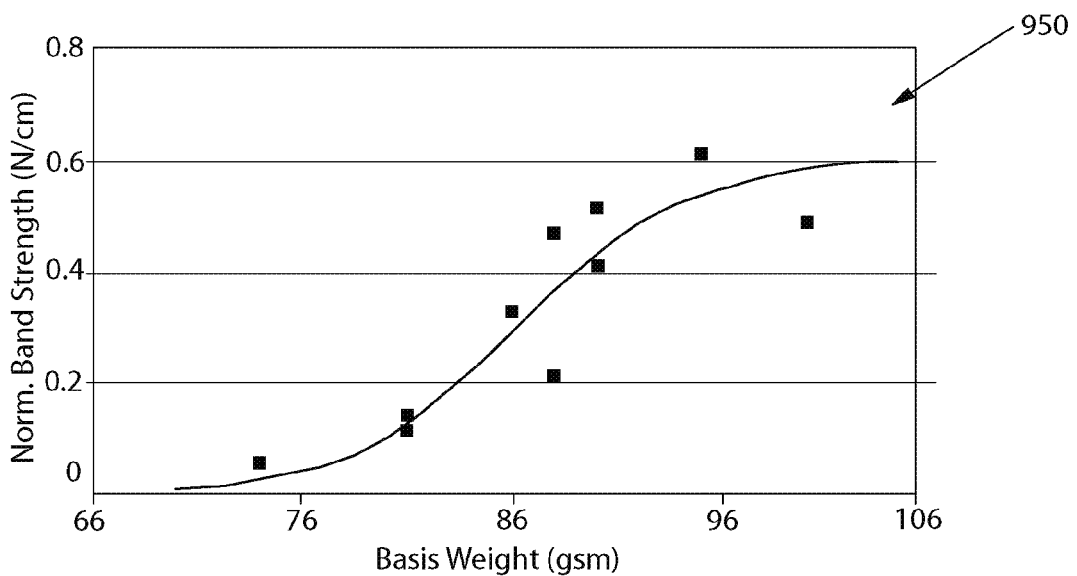
FIG. 14B is a representation of a graph depicting total basis weight versus normalized bond strength.

FIG. 14A shows a chart 900 that plots the distribution of the normalized bond strengths versus the total PE basis weight of the Examples. FIG. 14B shows a chart 950 that plots the distribution of the normalized bond strengths versus the total basis weight of the Examples. As can be seen in FIGS. 14A and 14B, the distribution results in an s-shaped curve that highlights the break between normalized bond strengths of greater than 0.4 N/cm and those below. The normalized bond strength values of the high pressure bonds between the first web 710 and the second web 720 for each of Examples 1-10 are shown in Table 1. Normalized bond strength is the average bond strength minus three standard deviations, and is calculated according to the Peel Test method below. Normalized bond strength is used because it is believed, without being limited by theory, that this value more accurately represents the probability that a suitable bond is present. Therefore, depending on the standard deviation of the average bond strength (e.g., up to 10% or even greater), an undesirable number of weak bonds may be present in a bonded portion of the laminate even though data indicates that the average bond strength of the bonded area is greater than the desired target (e.g., 0.4 N/cm). In such instances, a user of an article may be more likely to encounter a weak bond and be able to undesirably separate one or more components or portions of components from the article. For example, a leg band that is bonded to the outer cover of diaper and includes weak bonds may be more likely to be removed by a wearer such as a young child. The leg band or portion thereof may then be placed in an undesirable location such as the child's mouth, the floor, or the child's bedding. However, since normalized bond strength represents about 99.6% of the actual bonds present in the bonded area, the probability of a weak bond (i.e., a bond having a bond strength of less than 0.4 N/cm) being present is reduced.

TABLE 1

| Example # | First Nonwoven Layer of First Web Basis Wt (gsm) | First Nonwoven Layer of First Web (PP/PE) | Second Nonwoven Layer of First Web Basis Wt (gsm) | Second Nonwoven Layer of First Web (PP/PE) | Total Basis Wt of PE Film in Second Web (gsm) | Total Basis Weight (gsm) | Total PE Basis Weight (gsm) | Normalized Bond Strength (N/cm) |
|---|---|---|---|---|---|---|---|---|
| 1 | 20 | 50/50 | 18 | 70/30 | 36 | 74 | 51.4 | 0.06 |
| 2 | 25 | 50/50 | 20 | 70/30 | 36 | 81 | 54.5 | 0.14 |
| 3 | 20 | 50/50 | 25 | 50/50 | 36 | 81 | 58.5 | 0.12 |
| 4 | 25 | 50/50 | 25 | 50/50 | 36 | 86 | 61 | 0.33 |
| 5 | 20 | 70/30 | 18 | 70/30 | 50 | 88 | 61.4 | 0.21 |
| 6 | 20 | 50/50 | 18 | 70/30 | 50 | 88 | 65.4 | 0.47 |
| 7 | 20 | 50/50 | 20 | 70/30 | 50 | 90 | 66 | 0.41 |
| 8 | 20 | 50/50 | 20 | 70/30 | 50 | 90 | 66 | 0.52 |
| 9 | 20 | 70/30 | 25 | 50/50 | 50 | 95 | 68.5 | 0.61 |
| 10 | 25 | 50/50 | 25 | 50/50 | 50 | 100 | 75 | 0.49 |

As can be seen in Table 1, the total basis weight of the material in the bond area may not provide a suitable indication of whether or not a suitably strong bond (i.e., a bond having a normalized bond strength of greater than 0.4 N/cm) will be formed. For example, Examples 5 and 6 both contain about 88 gsm of material in the bond site; however, Example 6 has a higher PE basis weight than Example 5 (i.e., 65.4 gsm versus 61.4 gsm), and Example 6 provides a suitable bond while Example 5 does not (i.e., bond strength of 0.62 N/cm versus 0.53 N/cm, and normalized bond strength of 0.47 versus 0.21). As can be seen in Table 1, there is a clear demarcation between the suitable normalized bond strength of Example 6 and the unsuitable normalized bond strength of Example 5. Table 1 supports the belief that, while it is known that increasing the overall basis weight of the laminate may increase the bond strength, the basis weight of the PE in the laminate is at least partially responsible for determining the bond strength.

Test Methods

The following test methods utilize a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Hysteresis Test

1. Select a 2.54 cm (width)×7.62 cm (length) sample of the material for testing. In some cases, if it is not be possible to get a 2.54 cm×7.62 cm sample, a smaller sample may be used, but a gage length of 25 mm must still be used. If the sample is activated and/or includes an activated portion, the length of the sample is taken in the direction of activation.
2. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

3. Calibrate the tester according to the manufacturer's instructions.
4. Set the distance between the grips at 25 mm.
5. Place the sample in the flat surface of the jaws such that the longitudinal axis of the sample is substantially parallel to the gauge length direction. Mount the sample with minimal slack. Set the slack preload at 0.02 N/cm. This means that the data collection starts when the slack is removed with a force of 0.02 N/cm. Strain is calculated based on the adjusted gauge length ($l_{ini}$) which is the length of the sample in between the grips of the tensile tester at a force of 0.02 N/cm. This adjusted gauge length is taken as the initial sample length, and it corresponds to a strain of 0%. Percent strain at any point in the test is defined as the change in length in cm divided by the adjusted gauge length in cm times 100%.
6. a. First cycle loading: Pull the sample to a strain of 50% at a constant cross head speed of 254 mm/min.
   b. First cycle unloading: Hold the sample at 50% strain for 30 seconds and then return the crosshead to its starting position (0% strain) at a constant cross head speed of 254 mm/min. Hold the sample in the unstrained state for 1 minute.
   c. Set from second cycle loading: Pull the sample at a constant cross head speed of 254 mm/min, till it reaches a load of 0.05 N/25.4 mm (0.020 N/cm). Record the extended gauge length ($l_{ext}$). Next, return the crosshead to its starting position (zero strain) at a constant cross head speed of 254 mm/min. Set is defined as the strain at a second cycle load of 0.05 N/25.4 mm (0.020 N/cm). Calculate % set as indicated below.
   d. Second cycle unload: Next, return the crosshead to its starting position (zero strain) at a constant cross head speed of 254 mm/min.
      Percent Set is defined as the percent strain at a second cycle load of 0.05 N/25.4 mm (0.020 N/cm). Calculate % set as indicated below.

A computer data system records the force exerted on the sample during the test as a function of applied strain. From the resulting data generated, the following quantities are reported (note that loads are reported as force divided by the width of the sample and do not take into account the thickness of the sample):
1. Loads at 25% strain and 50% strain (N/cm)
2. % set (Percent Strain measured at a second cycle load of 0.02 N/cm);
3. % set=($l_{ext}$−$l_{ini}$)/$l_{ini}$*100%.

5 repetitions are done on each sample and the average and standard deviation reported.

Tensile Test
1. Perform steps 1-5 of the Hysteresis test as described above.
2. Then pull the sample at a constant cross head speed of 254 mm/min to 1000% strain (i.e., 11× the $l_{ini}$), or until the sample breaks.

The computer records the force exerted on the sample during the test as a function of applied strain. From the resulting data generated, report the following:
1. Loads at 25%, 50%, and 100% strain (N/cm)
2. Peak elongation (%) and peak load (N/cm).

5 repetitions are done on each sample and the average and standard deviation reported.

Peel Test
The purpose of the Peel Test is to measure the force required to separate two layers of a laminate structure. Environmental conditions for this test are 23° C. (±1° C.) and a relative humidity of 50% (±2%).

Equipment
   Universal constant rate of extension tensile testing machine with computer tester interface (e.g., Instron 4200, 4300, 4500 or 5500 series from Instron Engineering Corp.).
   Load cell chosen so that force results for the samples tested will be between 20 and 80% of the capacity of the load cell or load range used.
   Clamps that are appropriately sized to the sample dimensions to be tested (i.e., the width of the clamp is between 1-1.5× the width of the sample, and the clamping force is such that the clamp does not slip during testing).

Figure 15:
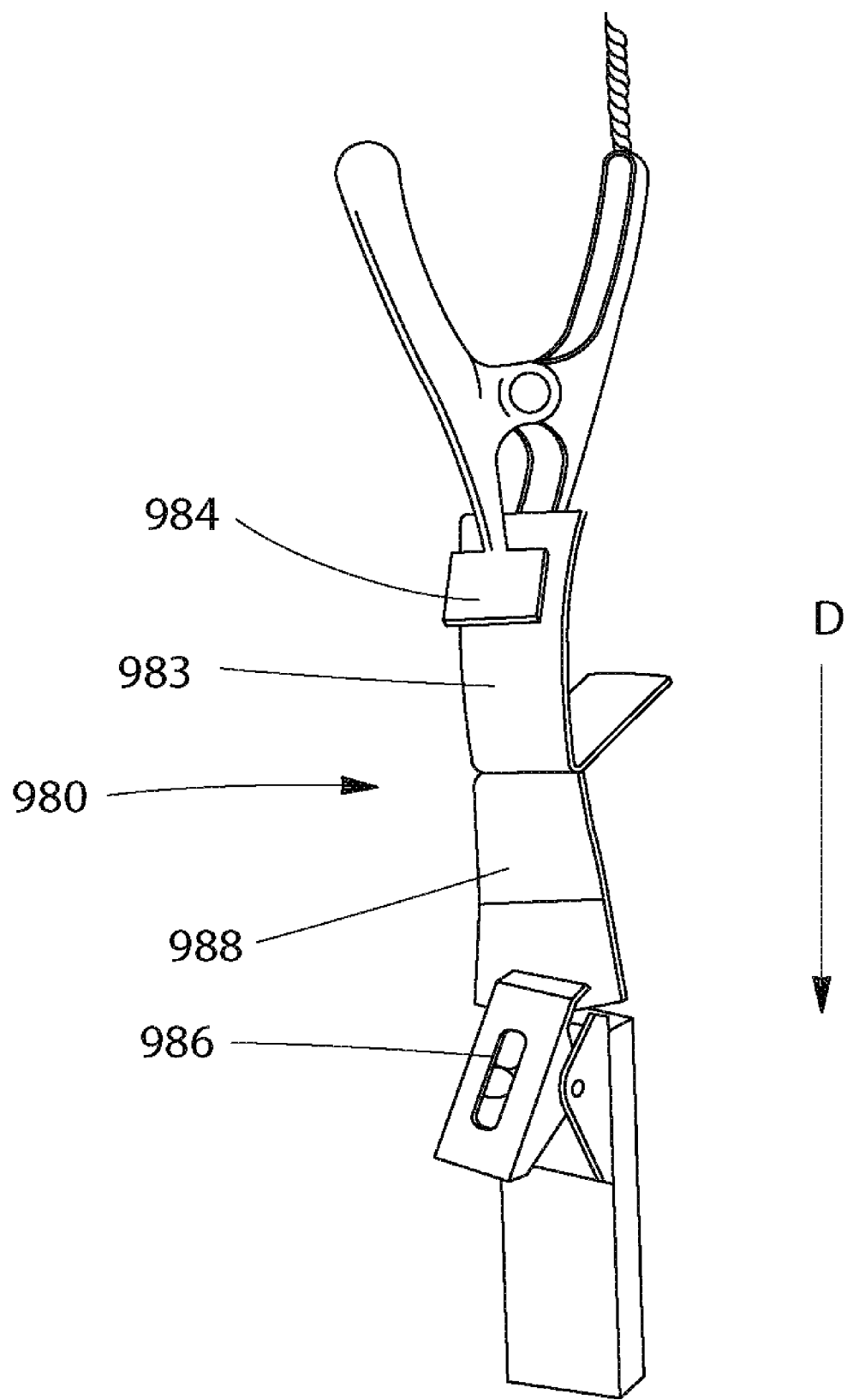
FIG. 15 illustrates portions of the Peel Test Method.

Procedure
FIG. 15 is provided to help illustrate portions of the Peel Test. An 18 cm long (i.e., in the test direction D) by 2.54 cm wide sample 980 is obtained (e.g., by cutting with scissors). Two adjacent layers 983 and 988, for which the bond strength is to be measured, are manually separated ("peeled") for a distance of about 2.5 cm in the test direction D taking care not to tear either layer 983, 988. Once the peel has been successfully started, find a region where both layers 983, 988 are intact and tearing has not occurred. Insert the free end of the first layer 988 of the sample 980 into the lower jaw 986 and close the lower jaw 986. Align the sample 980 between the lower jaw 986 and upper jaw 984. Insert the free end of the second layer 983 of the sample 980 into the upper jaw 984 and close the upper jaw 984. Essentially all of the slack in the sample 980 is eliminated, but less than 5 grams of force is applied to the load cell. The instrument is not zeroed after the sample 980 has been loaded. The tensile tester and the data collection device are started simultaneously as described by the manufacturer's instructions. If a sample 980 breaks or a layer tears before the test is finished, discard the sample 980 and make a new one.

Data Reporting
The results for the first 3 cm and the last 1 cm of peel are disregarded. The average peel force for the sample is calculated by the computer. The average peel force value is recorded. The bond strength for the sample equals the average peel force for the sample divided by the sample width and is reported in grams per centimeter. Ten repetitions are run for each sample (for a total of 10 bond strengths) and the bond strengths of the 10 repetitions are averaged and reported as average bond strength. The average bond strength values are converted to normalized bond strength by subtracting 3 times the standard deviation of the average bond strength, which is determined according to commonly accepted statistical practice, from the average bond strength value.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An outer cover for a disposable absorbent article, the outer cover comprising:
   a. a longitudinal direction, a lateral direction, a first longitudinal side edge and a second longitudinal side edge opposed thereto, a garment facing side and an opposing wearer facing side, a first waist region and a second waist region opposed thereto, wherein a portion of at least one of the first and second waist regions is activated in the lateral direction, a crotch region disposed between the first and second opposing waist regions, and a leg band portion disposed adjacent to at least one of the first and second longitudinal side edges in at least the crotch region, the leg band portion being activated in a direction other than the lateral direction;
   b. an extensible base layer, the base layer being coextensive with the outer cover in at least the longitudinal direction;
   c. an extensible reinforcing member, comprised of only nonwoven material, not activated, and joined to the base layer as an additional layer, the reinforcing member being disposed at least in the leg band portion of the crotch region of the outer cover;
   d. a leg band joined to at least one of the base layer and the reinforcing member in the leg band portion of the outer cover; and
   e. at least one elastic layer joined to the base layer in at least the first and second waist regions, the elastic layer(s) being absent in at least a portion of the crotch region.

2. The outer cover of claim 1, wherein the leg band is elastic.

3. The outer cover of claim 1, wherein the leg band portion includes a first sub-region and a second sub-region, the first sub-region being disposed adjacent to at least one of the first and second longitudinal side edges, and the second sub-region being disposed adjacent to and laterally inboard of the first sub-region in the crotch region of the outer cover.

4. The outer cover of claim 3, wherein the first and second sub-regions have different levels of activation.

5. The outer cover of claim 4, wherein the first sub-region has a higher level of activation than the second sub-region.

6. The outer cover of claim 1, wherein the base layer has a weight percentage of polyethylene based on the weight of the base layer and the reinforcing member has a weight percentage of polyethylene based on the weight of the reinforcing member and wherein the weight percentage of polyethylene of the reinforcing member is higher than the weight percentage of polyethylene of the base layer.

7. The outer cover of claim 6, wherein the base layer and the reinforcing member each comprise polypropylene and polyethylene and wherein the base layer and the reinforcing member have different polypropylene to polyethylene ratios.

8. The outer cover of claim 1, wherein at least one of the base layer and the reinforcing member is a nonwoven comprising core/sheath type bicomponent fibers.

9. The outer cover of claim 8, wherein the base layer comprises a nonwoven formed from core/sheath-type bicomponent fibers having a polypropylene core surrounded by a polyethylene sheath, the weight percent of polypropylene present in the nonwoven being 70% and the weight percent of polypropylene present in the nonwoven being 70%, based on the weight of the material.

10. The outer cover of claim 1, wherein the surface area of the reinforcing member is between about 20 and 60% of the surface area of the wearer-facing side of the base layer.

11. The outer cover of claim 1, the activated waist portion has a load at 50% strain of less than 2N/cm according to the Hysteresis Test.

12. The outer cover of claim 1, wherein the activated waist portion has a set of less than 15% according to the Hysteresis Test.

13. The outer cover of claim 1, wherein the total basis weight of the polyethylene in the base layer and reinforcing layer is at least 15 gsm.

14. The outer cover of claim 1, wherein the elastic layer is selected from the group of materials consisting of elastically stretchable films, laminates of elastically stretchable films and nonwovens, and elastic nonwovens.

15. The outer cover of claim 14, wherein the elastic layer comprises a laminate of an elastic film member joined to an extensible nonwoven member.

* * * * *

UNITED STATES PATENT AND TRADEMARK OFFICE
CERTIFICATE OF CORRECTION

| | | |
|---|---|---|
| PATENT NO. | : 8,333,748 B2 | Page 1 of 1 |
| APPLICATION NO. | : 12/398615 | |
| DATED | : December 18, 2012 | |
| INVENTOR(S) | : Desai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 770 days.

Signed and Sealed this
Eleventh Day of November, 2014

Michelle K. Lee
*Deputy Director of the United States Patent and Trademark Office*